(12) United States Patent
Taylor et al.

(10) Patent No.: US 10,073,037 B2
(45) Date of Patent: Sep. 11, 2018

(54) PLASMONIC JUNCTIONS FOR SURFACE-ENHANCED SPECTROSCOPY

(76) Inventors: Richard William Taylor, Cambridge (GB); Jeremy John Baumberg, Cambridge (GB); Sumeet Mahajan, Cambridge (GB); Tung-Chun Lee, Cambridge (GB); Oren Alexander Scherman, Cambridge (GB); Setu Kasera, Cambridge (GB); Roger Coulston, Cambridge (GB)

(*) Notice: Subject to any disclaimer, the term of this patent is extended or adjusted under 35 U.S.C. 154(b) by 1211 days.

(21) Appl. No.: 14/128,824

(22) PCT Filed: Jun. 24, 2011

(86) PCT No.: PCT/GB2011/000956
§ 371 (c)(1),
(2), (4) Date: Dec. 23, 2013

(87) PCT Pub. No.: WO2012/175900
PCT Pub. Date: Dec. 27, 2012

(65) Prior Publication Data
US 2014/0113382 A1    Apr. 24, 2014

(51) Int. Cl.
| | | |
|---|---|---|
| *G01N 33/553* | (2006.01) | |
| *G01N 21/65* | (2006.01) | |
| *G01N 33/543* | (2006.01) | |
| *B82Y 30/00* | (2011.01) | |
| *B82Y 40/00* | (2011.01) | |
| *B82Y 20/00* | (2011.01) | |
| *G01N 21/552* | (2014.01) | |

(52) U.S. Cl.
CPC ............ *G01N 21/658* (2013.01); *B82Y 20/00* (2013.01); *B82Y 30/00* (2013.01); *B82Y 40/00* (2013.01); *G01N 33/54346* (2013.01); *G01N 33/553* (2013.01); *G01N 21/554* (2013.01)

(58) Field of Classification Search
None
See application file for complete search history.

(56) References Cited

U.S. PATENT DOCUMENTS 7,867,391 B2 * 1/2011 Kim ................. G01N 33/54353
                                                 210/198.2
2009/0273779 A1   11/2009 Baumberg et al.

OTHER PUBLICATIONS

Taylor et al, "Precise Subnanometer Plasmonic Junctions for SERS within Gold Nanoparticle Assemblies Using Cucurbit[n]uril 'Glue'", ACSNANO, vol. 5, No. 5, published online Apr. 13, 2011, 3878-3887.*
Albrecht et al. "Anomalously Intense Raman Spectra of Pyridine at a Silver Electrode." Journal of the American Chemical Society, Jul. 1977, 99, pp. 5215-5217.
Alu et al. "Theory of linear chains of metamaterial/plasmonic particles as subdiffraction optical nanotransmission lines." Physical Review B, 2006, 74, 205436-1 to 205436-18.
An et al. "A general and efficient method to form self-assembled cucurbit[n]uril monolayers on gold surfaces." ChemComm, 2008, pp. 1989-1991.
Aslan et al. "Nanogold Plasmon Resonance-Based Glucose Sensing. 2. Wavelength-Ratiometric Resonance Light Scattering." Analytical Chemistry, Apr. 1, 2005, vol. 77, No. 7, pp. 2007-2014.
Aslan et al. "Controlled and Reversible Aggregation of Biotinylated Gold Nanoparticles with Streptavidin." Journal of Physical Chemistry B, 2004, 108, pp. 15631-15639.
Bernard et al. "Spectroscopy of Molecular Junction Networks Obtained by Place Exchange in 2D Nanoparticle Arrays." Journal of Physical Chemistry C, 2007, 111, pp. 18445-18450.
Bush, M.E. et al. "Charge-Mediated Recognition of N-Terminal Tryptophan in Aqueous Solution by a Synthetic Host." Journal of American Chemistry Society, 2005, 127, pp. 14511-14517.
Corma et al. "A pseudopolyrotaxane consisting in PPV threaded in multiple cucurbiturils." Tetrahedron Letters, 2007, 48, pp. 4613-4617.
Coulston et al. "Supramolecular gold nanoparticle-polymer composites formed in water with cucurbit[8]uril." ChemComm, 2011, 47, pp. 164-166.
Dammer et al. "Morphology and optical responses of SERS active π-conjugated poly (N-ethyl-2-ethynylpyridinium iodide)/ Ag nanocomposite systems." Physical Chemistry Chemical Physics, 2009, 11, pp. 5455-5461.
Daniel et al. "Gold Nanoparticles: Assembly, Supramolecular Chemistry, Quantum-Size-Related Properties, and Applications toward Biology, Catalysis and Nanotechnology." Chemical Reviews, 2004, 104, pp. 293-346.
De Waele et al. "Tunable Nanoscale Localization of Energy on Plasmon Particle Arrays." Nano Letters, 2007, vol. 7, No. 7, pp. 2004-2008.
Feldheim. "Assembly of Metal Nanoparticle Arrays Using Molecular Bridges." The Electrochemical Society Interface, 2001, pp. 22-25.
Fleischmann et al. "Raman Spectra of Pyridine Adsorbed at a Silver Electrode." Chemical Physics Letters, May 15, 1974, vol. 26, No. 2, pp. 163-166.
Florea et al. "Strong Binding of Hydrocarbons to Cucurbituril Probed by Flourescent Dye Displacement: A Supramolecular Gas-Sensing Ensemble." Angewandte Chemie International Edition, 2011, 50, pp. 9338-9342.
Frens. "Controlled Nucleation for the Regulation of the Particle Size in Monodisperse Gold Syspensions." Nature Physical Science, Jan. 1, 1973, vol. 241, pp. 20-22.

(Continued)

*Primary Examiner* — Chris L Chin
(74) *Attorney, Agent, or Firm* — Oliff PLC

(57) ABSTRACT

The invention relates to the use of a construct for the detection of an analyte using surface enhanced spectroscopic techniques. The construct includes linked surfaces, where the link is formed by a linker providing a fixed inter-surface separation between the linked surfaces, wherein the linker is a linking compound, and at least one of the surfaces is the surface of a nanoparticle. The linking compound is suitable for interacting with the analyte. The linking compound may be a cucurbituril. The surface enhanced spectroscopic technique may be surface enhanced Raman spectroscopy (SERS).

7 Claims, 20 Drawing Sheets

(56) References Cited

OTHER PUBLICATIONS

Ghosh et al. "Interparticle Coupling Effect on the Surface Plasmon Resonance of Gold Nanoparticles: From Theory to Applications." Chemical Reviews, 2007, 107, pp. 4797-4862.

Girard et al. "Theoretical Near-Field Optical Properties of Branched Plasmonic Nanoparticle Networks." Physical Review Letters, Sep. 8, 2006, 97, 100801-1 to 100801-4.

Graham, D. "The Next Generation of Advanced Spectroscopy: Surface Enhanced Raman Scattering from Metal Nanoparticles." Angewandte Chemie International Edition, 2010, 49, pp. 2-5.

Hao et al. "Electromagnetic fields around silver nanoparticles and dimers." Journal of Chemical Physics, Jan. 1, 2004, vol. 120, No. 1, pp. 357-366.

Harris et al. "Plasmonic Resonances of Closely Coupled Gold Nanosphere Chains." Journal of Physical Chemistry C, 2009, 113, pp. 2784-2791.

Hwang et al. "Noncovalent Immobilization of Protein on a Solid Surface by Cucurbit[7]uril-Ferrocenemethylammonium Pair, a Potential Replacement of Biotin-Avidin Pair." Journal of American Chemical Society, 2007, 129, pp. 4170-4171.

Jarvis et al. "Multiobjective evolutionary optimisation for surface-enhanced Raman scaterring." Anal. Bioanal. Chem., 2010, 397, pp. 1893-1901.

Jeanmaire et al. "Surface Raman Spectroelectrochemistry." J. Electroanal. Chem., 1977, 84, pp. 1-20.

Jiao et al. "A "green" method for isolation of cucurbit[7]uril via a solid state metathesis reaction." Chem. Commun., 2010, 46, pp. 2007-2009.

Kim, et al. "New Cucurbituril Homologues: Syntheses, Isolation, Characterization, and X-ray Crystal Structures of Cucurbit[n]uril (n=5,7, and 8)." Journal of American Chemical Society, 2000, 122, pp. 540-541.

Kneipp et al. "Single Molecule Detection Using Interface-Enhanced Raman Scattering (SERS)" Physical Review Letters, Mar. 3, 1997, vol. 78, No. 9, pp. 1667-1670.

Lagona et al. "The Cucurbit[n]uril Family" Angewandte Chemie International Edition, 2005, 44, pp. 4844-4870.

Lal et al. "Tailoring plasmonic substrates for surface enhanced spectroscopies." Chemical Society Review, 2008, 37, pp. 898-911.

Le et al. "Sub-wavelength localization of hot-spots in SERS." Chem. Phys. Lett., 2004, 396, pp. 393-397.

Lee et al. "Formation of dynamic aggregates in water by cucurbit[5]uril capped with gold nanoparticles." Chem. Commun., 2010, 46, pp. 2438-2440.

Li et al. "Organization of Inorganic Nanoparticles Using Biotin-Streptavidin Connectors." Chem. Mater., 1999, 11, pp. 23-26.

Li et al. "Dimers of Silver Nanosphere: Facile Synthesis and Their Use as Hot Spots for Surface-Enhanced Raman Scattering." Nano Letters, 2009, vol. 9, No. 1, pp. 485-490.

Liebsch et al. "Optical properties of small metallic particles in a continuous dielectric medium." J. Phys. C: Solid State, 1983, 16, pp. 5375-5391.

Lim et al. "Nanogap-engineerable Raman-active nanodumbbells for single-molecule detection." Nature Materials, Jan. 2010, 9, pp. 60-67.

Lin et al. "Universal diffusion-limited colloid aggregation." J. Phys: Condens. Matter, 1990, 2, pp. 3093-3113.

Lin et al. "Universal reaction-limited colloid aggregation." Physical Review A, Feb. 15, 1990, vol. 41, No. 4, pp. 2005-2020.

Mahajan et al. "Raman and SERS spectroscopy of cucurbit[n]urils." Physical Chemistry Chemical Physics, 2010, 12, pp. 10429-10433.

Miyahara et al. ""Molecular" Molecular Sieves: Lid-Free Decarnethylcucurbit[5]uril Absorbs and Desorbs Gases Selectively." Agnew. Chem. Int. Ed., 2002, vol. 41, No. 16, pp. 3020-3023.

Marquez et al. "Cucurbiturils: Molecular Nanocapsules for Time-Resolved Fluorescence-Based Assays." IEEE Transactions on Nanobioscience, Mar. 1, 2004, vol. 3, No. 1, pp. 39-45.

Martin et al. "Charged Gold Nanoparticles in Non-Polar Solvents: 10-min Synthesis and 2D Self-Assembly." Langmuir, 2010, 26, pp. 7410-7417.

Meakin, P. "Aggregation Kinetics." Physica Scripta, 1992, vol. 46, pp. 295-331.

Mohanty et al. "Ultrastable Rhodamine with Cucurbituril." Angewandte Chemie, 2005, 117, pp. 3816-3820.

Moskovits et al. "Adsorbate-Induced Silver Nanoparticle Aggregation Kinetics." The Journal of Physical Chemistry Letters, 2005, vol. 109, No. 31, pp. 14755-14758.

Moskovits, M. "Surface-enhanced spectroscopy." Reviews of Modern Physics, Jul. 1985, vol. 57, No. 3, pp. 783-828.

Myroshnychenko et al. "Modelling the optical response of gold nanoparticles." Chemical Society Review, 2008, 37, pp. 1792-1805.

Nie et al. "Probing Single Molecules and Single Nanoparticles by Surface-Enhanced Raman Scattering." Science, Feb. 21, 1997, 275, pp. 1102-1106.

Norman et al. "Near Infrared Optical Absorption of Gold Nanoparticle Aggregates." J. Phys. Chem. B, 2002, 106, pp. 7005-7012.

Park et al. "Structures of DNA-Linked Nanoparticle Aggregates." J. Phys. Chem. B, 2006, 110, pp. 12673-12681.

Quinten, M. "Optical Effects Associated with Aggregates of Clusters." Journal of Cluster Science, 1999, vol. 10, No. 2, pp. 319-358.

Rodriguez-Lorenzo et al. "Zeptomol Detection Through Controlled Untrasensitive Surface-Enhanced Raman Scattering." Journal of American Chemical Society, 2009, 131, pp. 4616-4618.

Schwartzberg et al. "Unique Gold Nanoparticle Aggregates as a Highly Active Surface-Enhanced Raman Scattering Substrate." J. Phys. Chem. B, 2004, 108, pp. 19191-19197.

Scott et al. "Harmonic Vibrational Frequencies: An Evaluation of Hartree-Fock, Moller-Plesset, Quadratic Configuration Interaction, Density Functional Theory, and Semiempirical Scale Factors." J. Phys. Chem., 1996, 100, pp. 16502-16513.

Sztainbuch, I.W. "The effects of Au aggregate morphology on surface-enhanced Raman scattering enhancement." The Journal of Chemical Physics, 2006, 125, 124707-1 to 124707-12.

Taylor et al. "Plasmonic junctions with cucurbit[5]uril 'glue': fabrication of precise sub-nm junctions in gold nanoparticle assemblies." Optical Society of America, May 1-6, 2011.

Weitz et al. "Fractal Structures Formed by Kinetic Aggregation of Aqueous Gold Colloids." Apr. 16, 1984, vol. 52, No. 16, pp. 1433-1437.

Wustholz et al. "Structure-Activity Relationships in Gold Nanoparticle Dimers and Trimers for Surface-Enhanced Raman Spectroscopy." Journal of American Chemical Society, 2010, 132, pp. 10903-10910.

Xu et al. "Electromagnetic contributions to single-molecule sensitivity in surface-enhanced Raman scattering." Physical Review E, Sep. 2000, vol. 62, No. 3, pp. 4318-4324.

Xu et al. "Spectroscopy of Single Hemoglobin Molecules by Surface Enhanced Raman Scattering." Physical Review Letters, Nov. 22, 1999, vol. 83, No. 21, pp. 4357-4360.

Mar. 2, 2012 International Search Report issued in European International Application No. PCT/GB2011/000956.

Jun. 24, 2011 Written Opinion in European Application No. PCT/GB2011/00956.

* cited by examiner

Figure 8 (a), (c) and (e)
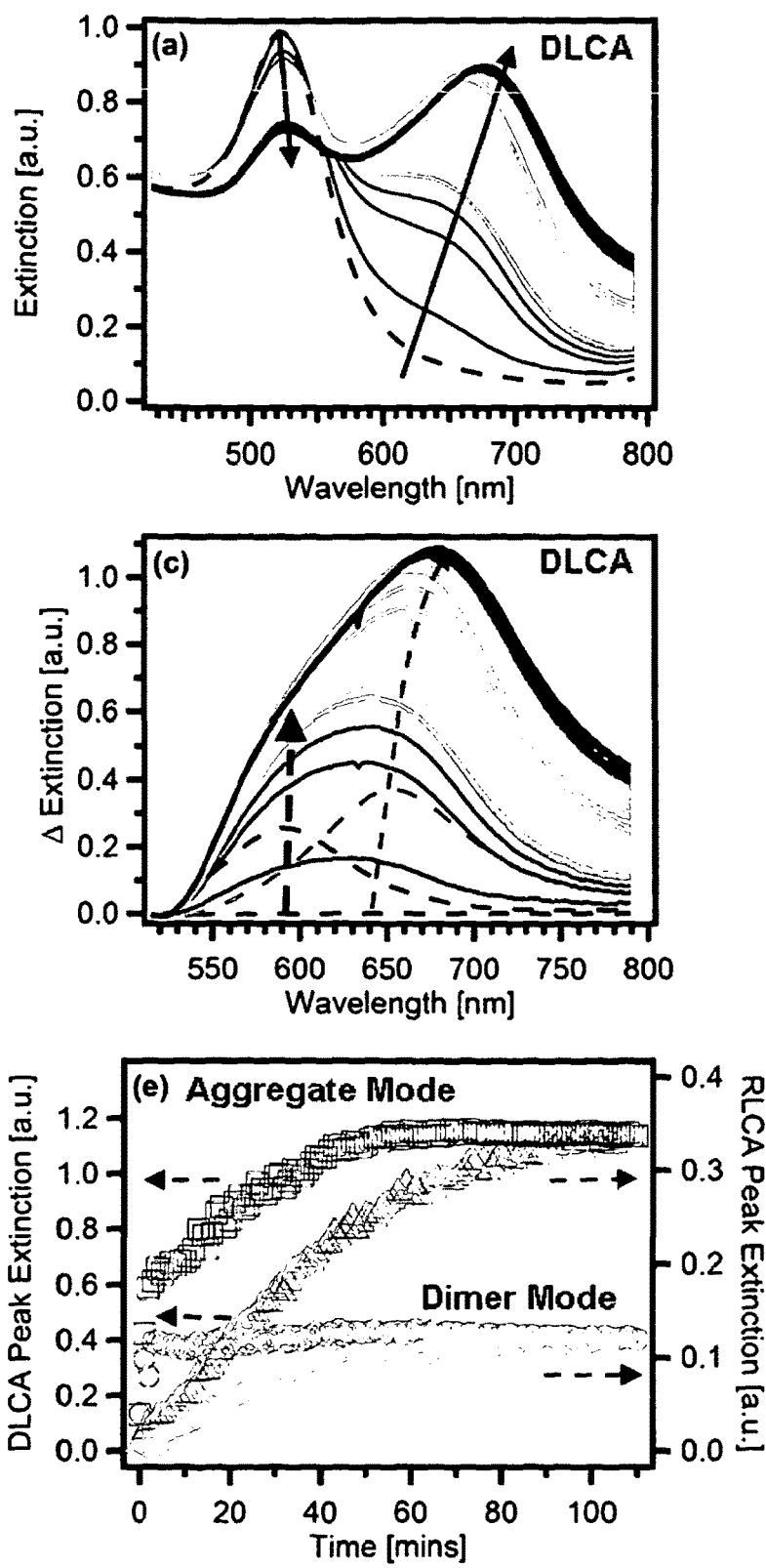

PLASMONIC JUNCTIONS FOR SURFACE-ENHANCED SPECTROSCOPY

PRIOR PUBLICATIONS

The present inventors acknowledge the publication of aspects of the present case in *Phys. Chem. Chem. Phys.* 2010, 12, 10429 published on 25 Jun. 2010, and *ACS Nano*, 2011, 5, 3878, published on 13 Apr. 2011, the contents of both of which are incorporated herein by reference in their entirety.

FIELD OF THE INVENTION

This invention relates to constructs for use in enhancing the detection of molecules using surface-enhanced spectroscopic techniques, as well the methods of detection, and methods for the preparation of constructs.

BACKGROUND

The discovery of enormous Raman signals from roughened silver electrodes along with understanding of the electric field enhancement mechanism sparked the promise of powerful surface-enhanced Raman spectroscopies (SERS) (see, for example, Fleischmann et al. *Chem. Phys. Lett.* 1974, 26, 442; Moskovits *Rev. Mod. Phys.* 1985, 57, 783; Albrecht et al. *J. Am. Chem. Soc.* 1977, 99, 5215; Jeanmaire et al. *J. Electroanal. Chem.* 1977, 84, 1; Mahajan et al. *Phys. Chem. Chem. Phys.* 2010, 12, 10429; Lal et al. *Chem. Soc. Rev.* 2008, 37, 898; Graham *Angew. Chem., Int. Ed.* 2010, 49, 2). In particular, SERS enhancements as high as $10^{10}$-$10^{14}$ derived from discrete gold nanocolloid assemblies, which amplify the electromagnetic field confined between closely coupled nanopairs, have permitted sensing of single molecules (see Schwartzberg et al. *J. Phys. Chem. B* 2004, 108, 19191; Hao et al. *J. Chem. Phys.* 2004, 120, 357; Kneipp et al. *Phys. Rev. Lett.* 1997, 78, 1667. Sztainbuch *J. Chem. Phys.* 2006, 125, 1. Le et al. *Chem. Phys. Lett.* 2004, 396, 393; Rodriguez-Lorenzo et al. *J. Am. Chem. Soc.* 2009, 131, 4616; Lim et al. *Nat. Mater.* 2010, 9, 60; Nie et al. *Science* 1997, 275, 1102; Xu et al. *Phys. Rev. Lett.* 1999, 4357; Xu et al. *Phys. Rev. E* 2000, 62, 4318; Wustholz et al. *J. Am. Chem. Soc.* 2010, 132, 10903). The ability to reproducibly control the interstitial regions of intense field amplification (so-called "hot spots") for reliable detection and identification of single molecules is an aim for those working in the field.

One of the most critical issues for achieving reproducible hot spots is the control of the gap size between plasmonic structures with subnanometer precision. Despite this, most work has concentrated more on the fabrication of the nanoparticles than control of these gaps. Control of the subnanometer critical dimension over large areas to create such hot spots uniformly is nontrivial. Even more difficult is placing precisely within these junctions of ultrahigh field enhancement. The simplest and most studied system for the generation of such hot spots is through aggregation of nanoparticle colloids. Although a huge under-standing of colloid aggregates exists due to numerous experimental, theoretical, and computational studies over the past 30 years (Myers *Surfaces, Interfaces and Colloids*; Wiley-VCH: New York, 1999; Chapters 4, 5, and 10; Creighton *Surface Enhanced Raman Scattering*; Chang, R. K., Furtak, T. E., Eds.; Plenum: New York, 1982; p 315; Meakin The Fractal Approach to Heterogeneous Chemistry; Avnir, D., Ed.; Wiley: New York, 1989; p 131; Weitz et al. *Phys. Rev. Lett.* 1984, 52, 1433; Girard et al. *Phys. Rev. Lett.* 2006, 97, 100801; De Waele et al. *Nano Lett.* 2007, 7, 2004; Harris et al. *J. Phys. Chem. C.* 2009, 113, 2784; Matsushita *The Fractal Approach to Heterogeneous Chemistry*, Avnir, D., Ed.; Wiley: New York, 1989; p 161) their widespread adoption as a practical SERS substrate has so-far been hindered by irreproducible performance (see Li et al. *Nano Lett.* 2009, 9, 485; Jarvis et al. *Anal. Bioanal. Chem.* 2010, 397, 1893).

For example, aggregates formed through the "salting" of citrate-capped colloids tend to display poor control over size, gap, and topology, while organic monolayer-capped assemblies exhibit inconsistent and broad particle spacing (FIG. 7a) (Novotny et al. Principles of Nano-Optics; Cambridge University Press: Cambridge, UK, 2006; pp 378-419; Bernard et al. *J. Phys. Chem. C* 2007, 111, 18445); supposedly, "rigid" linking molecules such as DNA, biotin-streptavidin, or multivalent thiols (FIG. 7b) (Park et al. *J. Phys. Chem. B* 2006, 110, 12673; Li et al. Chem. Mater. 1999, 11, 23; Aslan et al. *J. Phys. Chem. B* 2004, 108, 15631; Feldheim *Electrochem. Soc. Interface* 2001, 22; Dammer et al. *Phys. Chem. Chem. Phys* 2009, 11, 5455) restrict access to the hot spot they define and have not been rigid in practice.

Despite this vast amount of work on coagulation aggregates, crucial control over both particle spacing and the placement of molecules in these hot spots while linking the SERS to plasmon modes by simultaneous measurements has not been carried out.

SUMMARY OF THE INVENTION

The present inventors have identified a new construct that provides a fixed separation between surfaces, particularly nanoparticle surfaces. The surfaces are suitable for providing a surface enhanced resonance effect. The fixed separation is provided by a substantially rigid linker, comprising a linking compound, that connects the surfaces.

The construct provides reproducible plasmonics and is suitable for use in the detection of an analyte within the region between the surfaces. The construct is capable of localising the analyte, through interaction of the analyte with the linking compound, to the region of the construct that has the most intense confined electric field, thereby providing optimal sensing.

In a general aspect, the present invention provides improved methods for the detection of an analyte using surface enhanced spectroscopic techniques. The methods of the invention make use of a construct of linked surfaces, where the link is formed by a linker providing a constant inter-surface separation between the surfaces, thereby to provide an area between the surfaces that has enhanced characteristics for the detection of an analyte entering into that area. Each surface is suitable for providing a surface enhanced resonance effect.

In a first aspect of the invention there is provided a construct of linked surfaces, where the link is formed by a linker providing a constant inter-surface separation between the linked surfaces, wherein the linker comprises a linking compound and a molecule is bound to the linking compound, at least one of the surfaces is the surface of a nanoparticle, and each surface is suitable for providing a surface enhanced resonance effect.

The construct is suitable for providing a detectable signal that is indicative of the presence of the molecule that is bound to the linking compound. Such constructs are generated in the detection methods of the invention.

In a second aspect of the invention there is provided a method for the detection of an analyte, the method comprising the steps of:
(i) providing a test sample to be tested for the presence of an analyte;
(ii) contacting the test sample with a linking compound, which compound is suitable for linking surfaces, thereby to permit the linking compound to bind to analyte, where present;
(iii) subsequently providing a plurality of surfaces, and permitting the linking compound, optionally together with any analyte to which it is bound, to form a construct of linked surfaces, where the link is formed by a linker providing a constant inter-surface separation between the linked surfaces, wherein at least one of the surfaces is the surface of a nanoparticle, and each surface is suitable for providing a surface enhanced resonance effect; and
(iv) analysing the formed construct by a surface enhanced spectroscopic technique, thereby to detect the presence of any analyte bound to the linking compound;
or:
(i) providing a test sample to be tested for the presence of an analyte;
(ii) contacting the test sample with a construct of linked surfaces, where the link is formed by a linker providing a constant inter-surface separation between the linked surfaces, wherein the linker comprises a linking compound, at least one of the surfaces is the surface of a nanoparticle, and each surface is suitable for providing a surface enhanced resonance effect;
(iii) permitting the linking compound to bind to analyte, where present; and
(iv) analysing the formed construct by a surface enhanced spectroscopic technique, thereby to detect the presence of any analyte bound to the linking compound.

In a fourth aspect of the invention there is provided a method of preparing a construct, such as a construct according to the first aspect of the invention, the method comprising:
(i) providing a molecule;
(ii) contacting the molecule with a linking compound, which compound is suitable for linking surfaces, thereby to permit the linking compound to bind to the molecule; and
(iii) subsequently providing a plurality of surfaces, and permitting the linking compound, together with the molecule to which it is bound, to form a construct of linked surfaces, where the link is formed by a linker providing a constant inter-surface separation between the linked surfaces, wherein at least one of the surfaces is the surface of a nanoparticle, and each surface is suitable for providing a surface enhanced resonance effect; and
or:
(i) providing a molecule;
(ii) contacting the molecule with a construct of linked surfaces, where the link is formed by a linker providing a constant inter-surface separation between the linked surfaces, wherein the linker comprises a linking compound, at least one of the surfaces is the surface of a nanoparticle, and each surface is suitable for providing a surface enhanced resonance effect; and
(iii) permitting the linking compound to bind to the molecule.

In a further aspect of the invention there is provided the use of a construct as a binding partner for a molecule, wherein the construct comprises linked surfaces, where the link is formed by a linker providing a fixed inter-surface separation between the linked surfaces, wherein the linker is a linking compound, and at least one of the surfaces is the surface of a nanoparticle. The linking compound is suitable for interacting with the molecule.

In a further aspect there is provided a construct comprising linked surfaces, where the link is formed by a linker providing a fixed inter-surface separation between the linked surfaces, wherein the linker is a linking compound, and at least one of the surfaces is the surface of a nanoparticle. The compound is suitable for interacting with the molecule.

In each of the aspects above, the linking compound may be a host which is suitable for forming a host-guest complex with one or more of the molecules. In one embodiment, the linking compound is a cucurbituril.

DETAILED DESCRIPTION OF THE INVENTION

Figure 1:
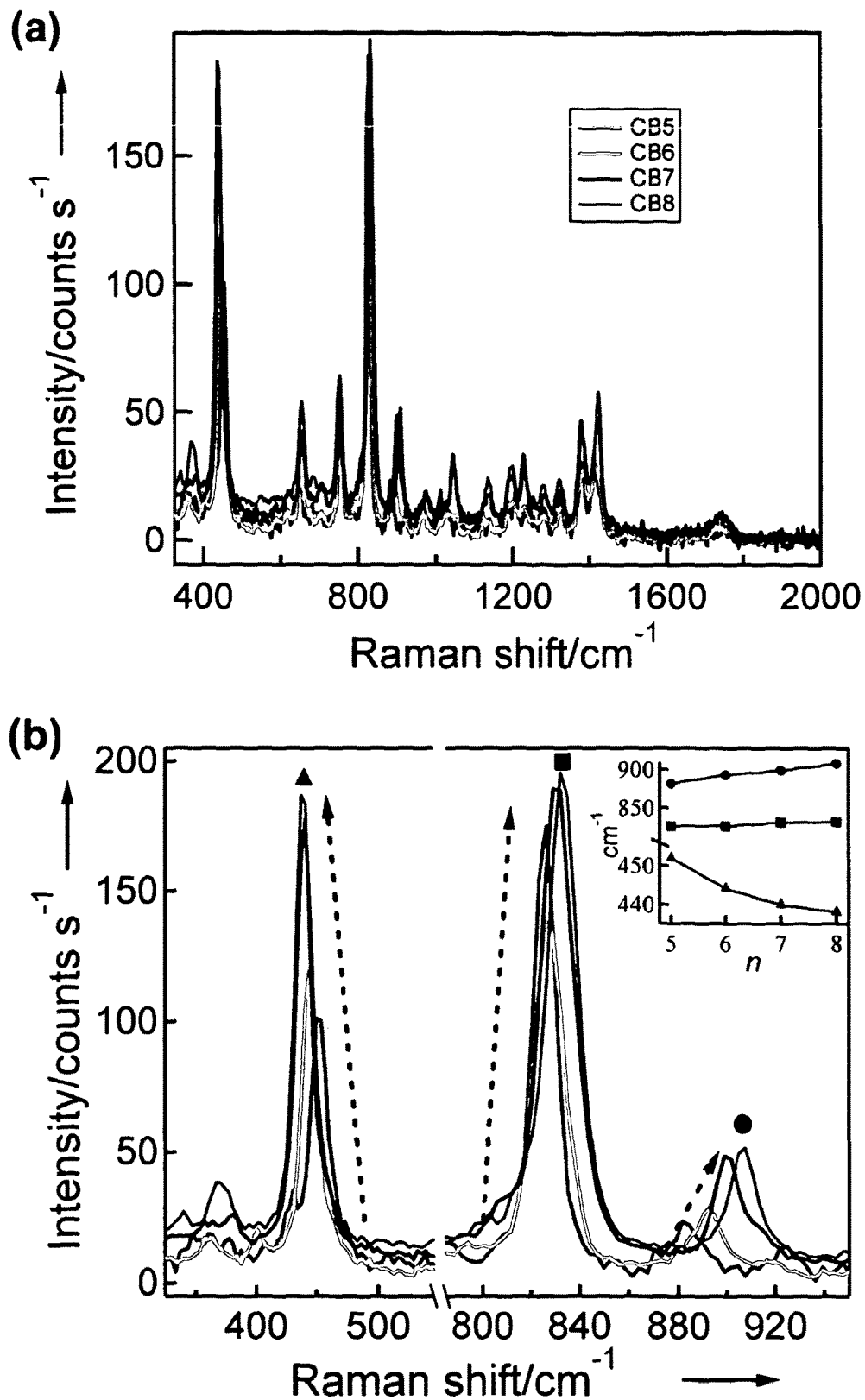
FIG. 1 (a) is a Raman spectra of CB[n=5-8] in the 'fingerprint' region; (b) is a close-up of the region 350 to 950 $cm^{-1}$ where it is observed that the peaks shift systematically with an increase in n. The variation of the marked peaks is shown in the inset. Acquisition conditions: 785 nm excitation, single 10 s scan.

The present inventors have shown that the modification of a surface by the adsorption of linkers and linking compounds produces partially controllable and highly consistent constructs, including aggregations. Crucially, these constructs maintain interparticle separations defined by the compound geometry, regardless of its concentration. This in turn allows for the consistent formation of distinct plasmon resonances. These advantages are available where the linker comprises a linking compound having a molecule, such as an analyte bound thereto.

Strong and reproducible surface enhanced spectroscopic effects are observed from such constructs with the linking compound itself acting as a spectroscopic reporter, where the exploited resonant plasmon modes can be tuned in spectral position and time through the concentration of the host and the nanoparticles present in the construct.

The present inventors have also provided a surface enhanced spectroscopic-based assay using the binding ability of the linking compound, in which an analyte molecule is subjected to intense field enhancement at the heart of a plasmonic hot spot. The work by the present inventors establishes a general use of nanoparticle-containing constructs as solution-based self-calibrated surface enhanced spectroscopic substrates in a range of selective sensing applications.

Construct

The present invention provides the use of a construct to permit the detection of an analyte. The construct comprises at least two surfaces which are suitable for providing a surface enhanced resonance effect. Of particular interest in the present case are those surfaces that are suitable for providing a surface enhancement for Raman spectroscopies (SERS). One of the surfaces is the surface of a nanoparticle.

The surfaces are linked by a linker, which comprise a linking compound. This link may be a non-covalent link. The connection between the surfaces, formed by the linker, may be referred to as a junction. The compound separates the surfaces of the junction by a constant distance. Thus, whilst the linker is connected to both surfaces, the distance between those surfaces at the junctions does not change. The provision of a system having a fixed gap between linked surfaces, as provided by the linker, is particularly advantageous as it provided reproducible, well-defined and predictable plasmonics.

Advantageously, the well-defined plasmon modes that arise due to the precise gap generated by the linking compound tune into resonance with common spectroscopic excitation wavelengths, and particularly with common Raman wavelengths.

A constant distance of separation may be obtained by the use of a linker, or a linking compound, that is substantially rigid. Linkers and linking compounds for use in the present invention are described in further detail below.

In one embodiment, the construct of the invention comprises linked surfaces, where the link is formed by a linker providing a fixed inter-surface separation between the linked surfaces. As described herein, this construct may disassociate in a process whereby the linker separates from one or both of the surfaces. The comments above made in relation to a fixed inter-surface distance is therefore a reference to the distance between those surfaces only when the linker is present and linked to both surfaces.

In the present case, the use of surface enhanced resonance spectroscopies makes use of the plasmonic characteristics of the junction, which may therefore also be referred to as a plasmonic junction.

In one embodiment, the construct includes a molecule, such as an analyte, which is bound to a linking compound. This construct may be analysed to detect the presence of the molecule analyte. Such a construct, which holds the analyte in a specific region of a junction, may also be useful for performing subsequent reaction steps, where the analyte is a reactant (or precursor) in that reaction step.

As described herein the molecule, once bound to a linking compound, may itself form a connection to one or both surfaces.

The proximity of the surface to one another provides an enhanced surface resonant effect. This effect is reduced beyond a separation of 100 nm. The most enhanced effects are seen at a separation of 10 nm and below.

The distance between the surfaces may be a value that is at least 0.7 nm, at least 0.8 nm, at least 0.9 nm, at least 1.0 nm, at least 1.5 nm, at least 2.0 nm.

The distance between the surfaces may be a value that is at most 100 nm, at most 80 nm, at most 60 m, at most 50 nm, at most 30 nm, at most 20 nm, at most 10 nm, at most 5.0 nm.

In one embodiment, the distance is in a range where the minimum and maximum values are selected from the embodiments above. For example, 0.8 to 10 nm.

In one embodiment, the distance between the surfaces is in the range 0.8 to 1.0 nm. In one embodiment, the distance between the surfaces is about 0.9 nm.

In one embodiment, the linking compound defines the gap between the surfaces. In one embodiment, the linking compound together with a bound molecule, such as an analyte, define the gap between the surfaces.

As described herein, cucurbituril is a suitable compound for linking surfaces, and reproducibly provides a gap of 0.9 nm.

The distance refers to the average spacing between the surfaces. The distance between surfaces may be measured using microscopic techniques, including TEM.

In one embodiment, the average spacing has a relative standard deviation (RSD) of at most 0.5%, at most 1%, at most 1.5%, at most 2%, at most 4%, at most 5%, at most 7%, at most 10%, at most 30% or at most 40%.

The relative standard deviation is calculated from the standard deviation divided by the numerical average and multiplied by 100.

In one embodiment, the relative standard deviation is about 30% or less.

The distance between the surfaces is referred to as a constant distance. Some degree of change in that distance is permitted, and may accommodate intramolecular movement within the linking molecule itself. Any such changes in the distance are limited to a change of at most 20%, at most 10%, or at most 5% of the constant inter-surface separation. Whilst such changes in the distance may be tolerated, it is preferred that the distance is substantially constant.

At its basic, the construct comprises surface of a nanoparticle and another surface, which may be the surface of another nanoparticle or the surface of a substrate. Particularly preferred are those constructs where both surfaces are the surfaces of nanoparticles.

The present invention also relates to constructs having multiple linked surfaces. Thus, each of the surfaces described may be linked to other surfaces by the linker. Thus, in one embodiment, the surface of the nanoparticle present in the construct may be linked to another surface by a linking surface. That other surface may the surface of a further nanoparticle. That further nanoparticle may in turn be linked by a linker to other nanoparticles. In this way, a construct comprising a plurality of linked surfaces is formed, wherein the linked surface are present on a plurality of nanoparticles. Where the construct takes this form of multiple interlinked surfaces, the construct may be referred to as an assembly. In the present invention the assembly typically comprises three or more nanoparticles.

Where multiple linkers are provided, some of the linkers may have a molecule bound thereto, and some may not.

Where an assembly is provided, the macrostructure of the assembly is not particularly limited. In one embodiment, the assembly may take the form of a substantially linear chain of interlinked constructs. Such forms may be obtainable using diffusion limited aggregation (DLCA). In another embodiment the assembly may take the form of a substantially clustered interlinked constructs. Such forms may be obtainable using reaction limited aggregation (RLCA).

The construct of the invention, including an assembly, is obtained or obtainable by the methods of preparation described herein.

Surfaces

The surfaces of the construct are suitable for providing a surface enhanced resonance effect. Thus, each surface provides an electric field enhancement. The combination of two surfaces, held together in close proximity, for example at 0.9 nm, thereby provides ultrahigh field enhancement at a region between the surfaces. This region may be referred to as a hotspot. Thus, the hotspot is an intense confined electric field. This hotspot may be used advantageously to detect the presence of an analyte in a sample, for example when the analyte is within the hotspot.

It is understood that the surfaces are discrete surfaces that are otherwise unconnected other than through the linking compound. The surfaces may be interlinked by a plurality of linking compounds. Additionally a surface may comprise one or more linking compounds that are connected to only one surfaces. Such linking compounds may result from the method of preparation where a linking compounds attaches to one surface but does not form a link to another surface within the time scale of the preparation reaction.

Linkers, and linking compounds, that are connected to only one surface may be referred to as singly capped. Those linkers, and linking compounds, that form a link between surfaces may be referred to as doubly capped.

The present invention relates to the use of linked surfaces, where one of the surfaces is a surface of a nanoparticle. The other surface may be the surface of a substrate or the surface of another nanoparticle.

The plasmon peak, λ max, for the construct is at least 350 nm, at least 400 nm, at least 450 nm or at least 500 nm.

The plasmon peak, λ max, for the construct is at most 800 nm, at most 750 nm, at most 700 nm or at most 650 nm.

The plasmon peak, λ max, may be obtained from UV-vis spectra of the construct.

In one embodiment, the plasmon peak, λ max, is a wavelength matched to the wavelength of the light used to analyse the construct, and particularly any linking compound or analyte present at the hotspot. Match may refer to a plasmon peak that is with 50, within 40, within 30, within 20, within 10 or within 5 nm of the wavelength of the light used to analyse the construct.

Nanoparticle

The use of nanoparticles as substrates for surface enhanced spectroscopy techniques is well studied. Any suitable nanoparticle that gives rise to a surface enhanced effect is suitable for use in the present invention.

Typically, the particle is a metal particle.

In one embodiment, the nanoparticle is or comprises a noble metal.

In one embodiment, the nanoparticle is or comprises a transition metal.

In one embodiment, the nanoparticle is a gold nanoparticle (AuNP) or a silver nanoparticle (AgNP), or a nanoparticle comprising both silver and gold.

Where the construct comprises two or more nanoparticles, for example where the construct is an aggregation, the nanoparticles may be the same or different. The differences may include differences in shape, size and/or composition amongst others.

The dimensions of the particle are chosen to give the most suitable plasmon peak of the construct.

In one embodiment, the nanoparticle has a diameter of at most 500 nm, at most 200 nm, at most 150 nm, at most 100 nm, at most 80 nm, or at most 70 nm.

In one embodiment, the nanoparticle has a diameter of at least 1 nm, at least 2 nm, at least 5 nm, at least 10 nm, at least 15 nm, at least 20 nm, at least 30 nm, or at least 40 nm.

In one embodiment, the diameter of the particle is in a range where the minimum and maximum rates are selected from the embodiments above. For example, the diameter is in the range 1 to 100 nm, or for example in the range 10 to 100 nm. For example, the diameter is in the range 2 to 500 nm In one embodiment, the nanoparticle has a diameter of about 20 nm.

The average refers to the numerical average. The diameter of a particle may be measured using microscopic techniques, including TEM.

The particles used in the present invention are sustainably monodisperse or have a very low dispersity. A narrow size distribution ensures that the scattering intensity is similar between particles, and therefore the surface enhanced effect is also similar.

In one embodiment, the particles have a relative standard deviation (RSD) of at most 0.5%, at most 1%, at most 1.5%, at most 2%, at most 4%, at most 5%, at most 7%, at most 10%, at moist 15%, at most 20% or at most 25%.

In one embodiment, the particle has a hydrodynamic diameter of at least 5 nm, at least 10 nm, at least 15 nm, at least 20 nm, at least 30 nm, at least 40 nm.

In one embodiment, the particle has a hydrodynamic diameter of at most 500 nm, at most 200 nm, at most 150 nm, at most 100 nm, at most 80 nm, or at most 70 nm. The hydrodynamic diameter may refer to the number average or volume average. The hydrodynamic diameter may be determined from dynamic light scattering (DLS) measurements of a particle sample.

The size of the particle and the composition of the particle may be selected to provide the most appropriate or beneficial surface enhanced effect.

Gold and silver particles may be prepared using techniques known in the art. Examples of preparations include those described by Coulston (Coulston et al *Chem. Commun.* 2011, 47, 164) and Martin (Martin et al. *Langmuir* 2010, 26, 7410) and Frens (Frens *Nature Phys. Sci.* 1973, 241, 20), which are incorporated herein by reference in their entirety.

The linking compound may be present when the nanoparticle is constructed. The linking compound may be used to influence the formation of the final nanoparticle form, for example, with regards to the assize of the final particle. The use of cucurbituril to influence the formation of a nanoparticle is described by Lee et al. *Chem. Commun.* 2010, 46, 2438.

Generally, the particle is substantially spherical. However, particles having other shapes may be used, if appropriate or desirable.

Substrate

In one embodiment, the surface is the surface of a substrate. Typically, the surface is a rough surface. The surface may be characterised by the presence of protrusions and/or recesses. The surface topography may be characterised by the presence of polyhedra, holes and/or wells. The surface may have a substantially regular pattern of such characterising features.

Suitable substrates for sue in the present case include those described in US 2009/0273779.

In one embodiment, the surface is a gold- or silver-coated surface, or a mixture of both.

Substrates that are capable of providing a surface enhanced resonant effect are well known to those of skill in the art. Surfaces are available from commercial sources, and one such surface for use in the present invention includes Klarite™, a SERS substrate, which is available from Renishaw Diagnostics.

Linker

The construct of the invention is provided with surfaces that are held at a constant inter-surface separation. A linker may be provided to link these surfaces and hold them at this fixed distance apart.

In one embodiment, the linker comprises a linking compound.

In one embodiment, the linker comprises a linking compound having a molecule, which may be an analyte, bound thereto. In this embodiment, the molecule may itself be linked to a surface, and the molecule and the linking compound may define the constant inter-surface separation. Here, the molecule may be directly linked to a surface.

Alternatively, the linking compound alone may define the constant inter-surface separation. In this case, the molecule is bound to the linking compound, but it is not itself directly linked to a surface.

In one embodiment, the linker comprises a linking compound, wherein the linking compound is not bound to a molecule, such as an analyte. In this embodiment, the linker is a linking compound.

Linking Compound

A linking compound is provided to separate the surfaces in the construct. The linking compound is capable of providing a fixed, or constant, distance of separation between those surfaces. Typically, the linking compound is substantially rigid. Thus, when the linking molecule links the surfaces, its rigidity limits or prevents relative movement of a surface to or from the other surface.

In one embodiment, the linking compound forms a non-covalent link to each surface, or it is suitable for forming such a link.

In one embodiment, the linking compound has a molecule, such as an analyte, bound to it, and the linking compound, optionally together with the molecule, forms a non-covalent link to each surface, or it is suitable for forming such a link.

Where a molecule is bound to the linking compound, the linking compound may form a non-covalent link to one surface, and the molecule may form a non-covalent link to the other surface. In this embodiment, the linking compound may optionally provide a bonding contribution to the other surface i.e. the connection to the other surface may be a combination of bonding interactions of the linking compound and the molecule.

The linking compound may interact with a molecule such as an analyte. The linking compound is suitable for binding with the analyte. Such binding holds the analyte at the plasmonic junction, at the gap between the surfaces that has the most intense confined electric field (the hot spot). It is not necessary that the linking compound itself be detectable by the surface enhanced spectroscopic technique that is used to detect the analyte. However, it is beneficial for the use of the construct that the linking compound be spectroscopically active.

The present invention extends to the use of linking compounds that are suitable for simultaneously binding two or more molecules. These molecules may be the same or they may be different.

The interaction between a molecule and the linking compound may be a non-covalent interaction.

The linking compound may be chosen on the basis of the analyte to be detected. The selection may be based on the binding affinity of the host with the analyte.

Where the linking compound binds to a single molecule, such as a single analyte molecule, the association constant, $K_a$, for the resulting complex is at least $10^2$ $M^{-1}$, at least $10^3$ $M^{-1}$, of at least $10^4$ $M^{-1}$, of at least $10^5$ $M^{-1}$, of at least $10^6$ $M^{-1}$, of at least $10^7$ $M^{-1}$, of at least $10^8$ $M^{-1}$, of at least $10^9$ $M^{-1}$, of at least $10^{10}$ $M^{-1}$, of at least $10^{11}$ $M^{-1}$, or of at least $10^{12}$ $M^{-1}$.

In one embodiment, the linking compound and the molecule are capable of forming a complex which has an association constant in the range $10^4$ to $10^7$ $M^{-1}$.

Where the linking compound binds to two molecule, such as two analyte molecules, the association constant, $K_a$, for that complex is at least $10^4$ $M^{-2}$, of at least $10^5$ $M^{-2}$, of at least $10^6$ $M^{-2}$, at least $10^7$ $M^{-2}$, at least $10^8$ $M^{-2}$, at least $10^9$ $M^{-2}$, at least $10^{10}$ $M^{-2}$, at least $10^{11}$ $M^{-2}$, or at least $10^{12}$ $M^{-2}$. The association constant refers to the rate at which the second molecule binds to (disassociates from) the intermediate complex of the linking compound and the first molecule.

In one embodiment, the linking compound is active in the surface enhanced spectroscopy technique employed. For example, the host may be Raman-active.

In one embodiment, the linking compound is chosen such that the signals generated in the surface enhanced spectroscopy technique do not overlap with those generated by the analyte.

Particularly suitable for use in the present invention is a host compound. A host compound has a cavity (which may be a through cavity) which is capable of holding (hosting) at least part of a guest within. This may be referred to as a guest-host complex. The host compound may take the form of a cage structure. Hosts are suitable for providing the constant distance between linked surfaces owing to the intrinsic rigidity of the host form.

In one embodiment, where a molecule is bound to a host, the molecule may wholly contained within the cavity of that host. In this embodiment, the host alone will form the link between the surfaces.

In one embodiment, where a molecule is bound to a host, the molecule may not be wholly contained within the cavity of that host. Here, part of the molecule may extend out of the cavity. This part of the molecule may be capable of forming a bonding interaction with a surface. In this embodiment, the host together with the molecule may form the link between the surfaces. For example, the host may form the connection to one surface, and the molecule (or more specifically, the part of the molecule extending out of the cavity) may form the connection to the other surface. As noted above, is such an embodiment, the linking compound may optionally provide a bonding contribution to the other surface i.e. the connection to the other surface may be a combination of bonding interactions of the linking compound and the molecule.

The host may be capable of holding one, two or more guests within.

The host may be a supramolecular macrocycle. Suitable compounds for use include cucurbituril, cyclodextrin and calixarene.

In one embodiment, the host is a cucurbituril, as described below.

In one embodiment, the linking compound is a rod, and the analyte is capable of binding to an outer surface of the rod.

Cucurbituril

In one embodiment, the host is a cucurbituril. Such hosts are particularly suitable for use in the present invention owing to their ready commercial availability in different cavity sizes, their well studied and reported ability to complex with a variety of guest compounds, in both binary and ternary complexes (Marquez, et al. *IEEE Trans. Nanobiosci.* 2004, 3, 39; Mohanty et al. *Angew. Chem.* 2005, 117, 3816; Lagona et al. *Angew. Chem., Int. Ed.* 2005, 44, 4844).

Cucurbiturils are also useful owing to the fact that the members of the cucurbituril family are capable of providing a fixed separation distance between surfaces. Moreover, the cucurbituril members are able to provide the same separation, of 0.9 nm, between surfaces.

Cucurbituril compounds are also spectroscopically active, including Raman active (Miyahara et al. *Phys. Chem. Chem. Phys.* 2010, 12, 10429). Thus, cucurbituril can act as a physical link between surfaces, yet it can also allow local reporting of the field confinement within the centre of junction by virtue of its own spectroscopic activity.

Cucurbituril compounds are also capable of binding to one or more compounds with binding affinities such as those set out above.

Some of the present inventors have demonstrated that cucurbituril compounds bind to metal surfaces, including the surfaces of gold nanoparticles. See, for example, Lee et al. *Chem. Commun.* 2010, 46, 2438.

Figure 7:
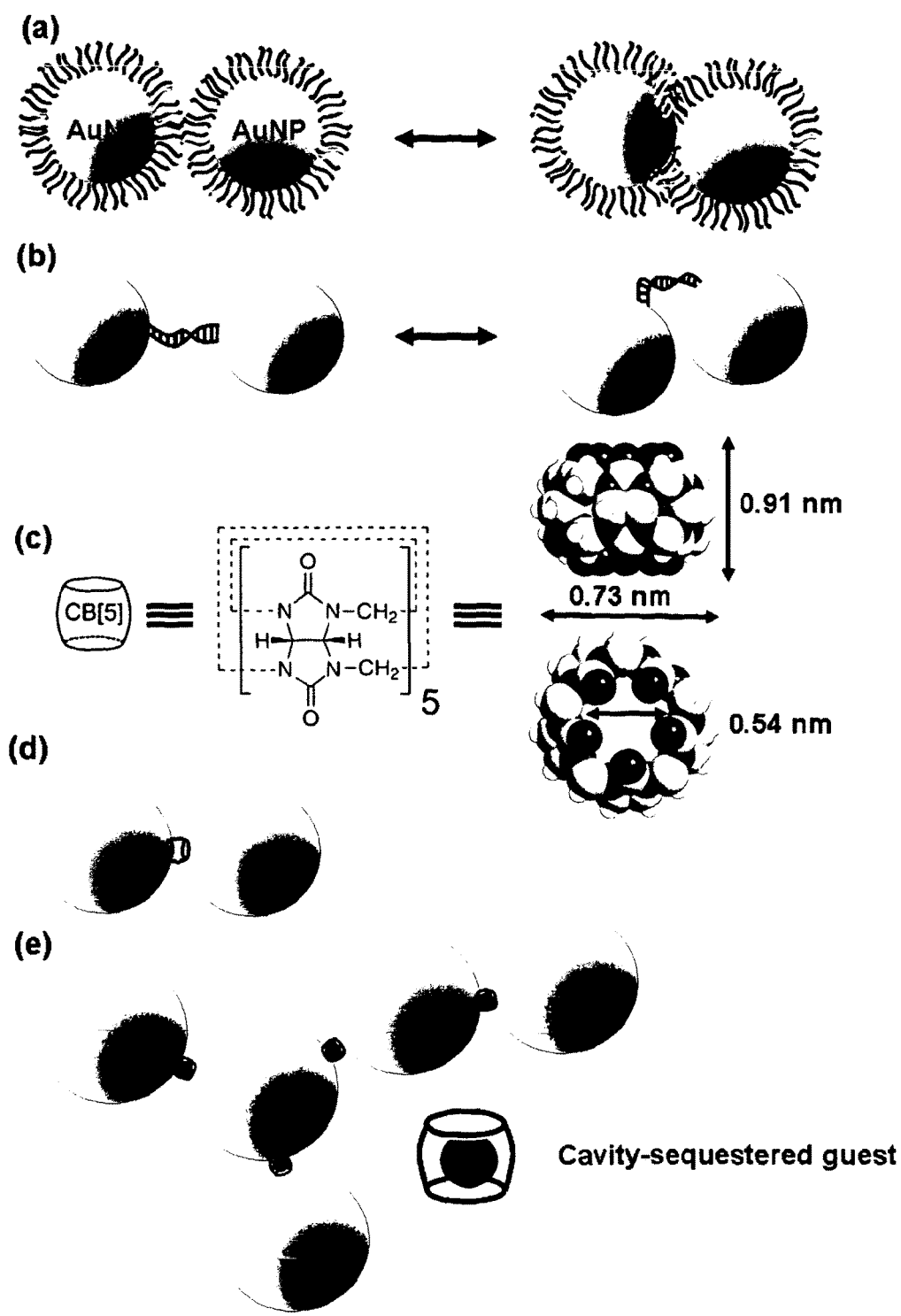
FIGS. 7 (a) and (b): Current strategies to generate a coagulate of AuNPs produce inconsistent and uncontrollable interparticle spacing through (a) organic-capped colloids or (b) DNA-mediated linkers. (c) Cucurbit[5]uril composed of five cyclically arranged glycoluril units, with a hydrophobic internal cavity and polar carbonyl portals that bind to the Au surface. (d) AuNPs glued into a dimer by CB[n] with portal-to-portal separation rigidly fixed at 0.9 nm. No other binding configuration is possible. (e) CB[n] cavity supports selective guest sequestration, leading to the use of AuNP: CB[n] aggregates for molecular-recognition-based SERS assays where the CB-[n] defines the nanojunctions.

Cucurbituril compounds are well known. Cucurbit[8]uril (CB[8]; CAS 259886-51-6) is a barrel shaped container molecule which has eight repeat glycoluril units and an internal cavity size of 479 $Å^3$ (see structure below and FIG. 7(C) which shows CB[5]). CB[8] is readily synthesised using standard techniques and is available commercially (e.g. Sigma-Aldrich, Mo. USA).

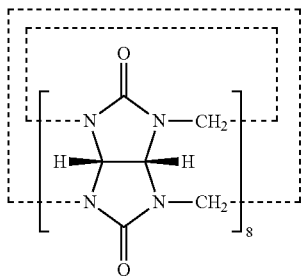

In other aspects of the invention, cucurbituril variants and derivatives are provided and find use in the methods described herein. Such may be referred to generically as cucurbituril compounds.

Cucurbituril compounds are known to bind to metal surfaces through the carbonyl portals (An et al. *Chem. Commun.* 2008, 1989; Lee et al. *Chem. Commun.* 2010, 2438). The construct of the present invention is formed by the binding of the carbonyls groups at either end of the molecule thereby to doubly cap the cucurbituril.

The van der Waal's dimension of cucurbituril from carbonyl portal to carbonyl portal, as established by XRD measurements, is 0.91 nm (see, for example, Lee et al. *Chem. Commun.* 2010, 46, 2438), which is consistent with the finding that cucurbiturils provide an inter-surface separation between the linked surfaces of about 0.9 nm.

Cucurbituril compounds are particular attractive for use owing to the common portal to portal distance for each family member (Marquez, et al. *IEEE Trans. Nanobiosci.* 2004, 3, 39; Mohanty et al. *Angew. Chem.* 2005, 117, 3816; Lagona et al. *Angew. Chem., Int. Ed.* 2005, 44, 4844). Thus cucurbituril linking compounds may be interchanged, for example to take into account binding associations with different molecules, yet the similar inter-surface spacing will provide predictable surface effects.

In one embodiment, the cucurbituril is selected from the group consisting of CB[5], CB[6], CB[7], CB[8], CB[10], and CB[12].

In one embodiment, the cucurbituril is a CB[6], CB[7], or CB[8].

In one embodiment, the cucurbituril is a CB[7].
In one embodiment, the cucurbituril is a CB[5].
In one embodiment, the cucurbituril is a CB[8].
In one embodiment, references to the cucurbiturils above are references to variants and derivatives thereof.
In one embodiment, the cucurbituril is not CB[5].

A variant of CB[8] may include a structure having one or more repeat units that are structurally analogous to glycoluril. The repeat unit may include an ethylurea unit. Where all the units are ethylurea units, the variant is a hemicucurbituril. The variant may be a hemicucurbit[12]uril (shown below, see also Lagona et al. *Angew. Chem. Int. Ed.* 2005, 44, 4844).

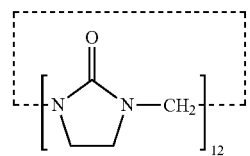

In other aspects of the invention, cucurbituril derivatives are provided and find use in the methods described herein. A derivative of a cucurbituril is a structure having one, two, three, four or more substituted glycoluril units. A substituted cucurbituril compound may be represented by the structure below:

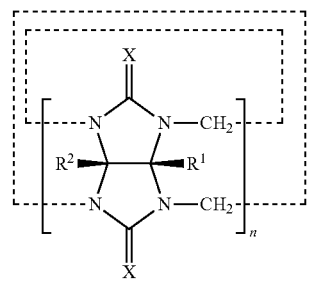

wherein:
n is an integer of at least 5;
and for each glycoluril unit
each X is O, S or $NR^3$, and
—$R^1$ and —$R^2$ are each independently selected from —H and the following optionally substituted groups: —$R^3$, —OH, —$OR^3$, —COOH, —$COOR^3$, —$NH_2$, —$NHR^3$ and —$N(R^3)_2$ where —$R^3$ is independently selected from $C_{1-20}$alkyl, $C_{6-20}$-carboaryl, and $C_{5-20}$heteroaryl, or where —$R^1$ and/or —$R^2$ is —$N(R^3)_2$, both —$R^3$ together form a $C_{5-7}$ heterocyclic ring; or together —$R^1$ and —$R^2$ are $C_{4-6}$alkylene forming a $C_{6-8}$-carbocyclic ring together with the uracil frame.

In one embodiment, one of the glycoluril units is a substituted glycoluril unit. Thus, —$R^1$ and —$R^2$ are each independently —H for n−1 of the glycoluril units In one embodiment, n is 5, 6, 7, 8, 10 or 12.
In one embodiment, n is 8.
In one embodiment, each X is O.
In one embodiment, each X is S.
In one embodiment, $R^1$ and $R^2$ are each independently H.
In one embodiment, for each unit one of $R^1$ and $R^2$ is H and the other is independently selected from —H and the following optionally substituted groups: —$R^3$, —OH, —$OR^3$, —COOH, —$COOR^3$, —$NH_2$, —$NHR^3$ and —$N(R^3)_2$. In one embodiment, for one unit one of $R^1$ and $R^2$ is H and the other is independently selected from —H and the following optionally substituted groups: —$R^3$, —OH, —$OR^3$, —COOH, —$COOR^3$, —$NH_2$, —$NHR^3$ and —$N(R^3)_2$. In this embodiment, the remaining glycoluril units are such that $R^1$ and $R^2$ are each independently H.

Preferably —$R^3$ is $C_{1-20}$alkyl, most preferably $C_{1-6}$alkyl. The $C_{1-20}$alkyl group may be linear and/or saturated. Each group —$R^3$ may be independently unsubstituted or substituted. Preferred substituents are selected from: —R$^4$, —OH, —SH, —SR$^4$, —COOH, —COOR$^4$, —NH$_2$, —NHR$^4$ and —N(R$^4$)$_2$, wherein —R$^4$ is selected from C$_{1-20}$alkyl, C$_{6-20}$-carboaryl, and C$_{5-20}$heteroaryl. The substituents may be independently selected from —COOH and —COOR$^4$.

In some embodiments, —R$^4$ is not the same as —R$^3$. In some embodiments, —R$^4$ is preferably unsubstituted.

Where —R$^1$ and/or —R$^2$ is —OR$^3$, —NHR$^3$ or —N(R$^3$)$_2$, then —R$^3$ is preferably C$_{1-6}$alkyl. In some embodiments, —R$^3$ is substituted with a substituent —OR$^4$, —NHR$^4$ or —N(R$^4$)$_2$. Each —R$^4$ is C$_{1-6}$alkyl and is itself preferably substituted.

Analyte

The present invention provides techniques for the detection of an analyte within a sample.

At its broadest, the present invention provides a construct comprising a plurality of linked surfaces, where the link is formed by a linker providing a fixed inter-surface separation between the linked surfaces, wherein the linker is a linking compound, and at least one of the surfaces is the surface of a nanoparticle The space defined by the linker is a hot spot for improved surface enhanced spectroscopic techniques. An analyte present or entering into that hot spot may be detected. The analysis of that analyte is assisted by the binding of that analyte to the linking compound, thereby to hold the analyte in the hotspot region for the timescale of the surface enhanced spectroscopic technique.

In one embodiment, the analyte binds to the linking compound, and this binding is detectable by surface enhanced spectroscopy. A binding event may be detected by a shift in a signal of the linking compound, or an interaction may be detected by the appearance of a new signal associated with the guest, or both. The signal is a signal from a surface enhanced spectroscopic technique, such as surface enhanced Raman spectroscopy.

A reference to a molecule herein, may be a reference to an analyte. Similarly, a reference to an analyte may be construed more broadly as a reference to a molecule.

In one embodiment the analyte is a guest for a host. The guest is capable of interacting with the host in a cavity of the host. The interaction is a non-covalent interaction.

The analyte is any compound that is capable of forming a complex with the host. As described herein, the analyte compound binds to a linking compound, and together with the linking compound the analyte may form the link between the surfaces. Thus, in one embodiment, the analyte itself may be connected to a surface. Here, the analyte may be provided with functionality that is suitable for forming a bonding interaction with a surface.

Typically, the interaction of the analyte with the surface is weak compared to that of the linking compound.

The analyte may be a small molecule, and this may include gas molecules such as N$_2$, O$_2$, N$_2$O, NO, CO, CO$_2$ and CH$_4$. Hosts, such as CB[5] can readily bind to gas molecules of this type (see Mahajan et al. *Angew. Chem. Int. Ed.*).

The analyte may be a natural product.

The analyte may be a metabolite.

In one embodiment, the analyte is a neurotransmitter, such as dopamine (DA) and serotonin (5-HT, 5-hydroxytryptamine).

Where the host has a cavity, the cavity may be suitably large to entirely contain the analyte.

In one embodiment, the molecular weight of the analyte may be at most 1,000, 500, 400, 300, 200, 100 or 50.

The analyte may be provided in a test sample. Typically the sample is an aqueous sample.

The methods of detection of the present invention permit an analyte to be detected at very low concentrations, to the extent that the techniques described herein may be used at the single molecule level of detection.

Cucurbituril Guests

In one embodiment, the present invention relates to the use of cucurbituril as a linking compound. Molecules and structural groups that are capable of forming a complex with cucurbituril are well known.

A curcubtirul guest molecule may be derived from, or contain, a structure from the table below:

| | Guest Molecules |
|---|---|
| A1 | HO—naphthalene—OH |
| A2 | HO—naphthalene |
| A3 | phenylalanine structure (benzyl-CH(NH$_2$)-COOH) |
| A4 | tyrosine structure (HO-phenyl-CH$_2$-CH(NH$_2$)-COOH) |
| A5 | tryptophan structure (indole-CH$_2$-CH(NH$_2$)-COOH) |
| B1 | 4,4'-bipyridinium (methyl viologen-like) |
| A6 | 2,6-bis(imidazolinyl)naphthalene |
| A7 | HO-phenyl-CH$_2$-piperazine-NH |

-continued

| Guest Molecules |
|---|
| A8 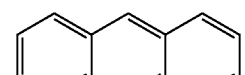 |
| A9 |
| A10 |
| A11 |
| A12 |
| B2 |
| B3 |
| B4 |
| A13 |
| A14 |

-continued

| Guest Molecules |
|---|
| A15  |
| A16 | where the structure may be a salt, including protonated forms, where appropriate. In one embodiment, the guest molecules are guest molecules for CB[8].

In one embodiment, the guest molecule is, or is derived from, or contains, structure A1, A2, or A13 in the table above.

In some embodiments, first and second guest molecules form a pair which may interact within the cavity of cucurbituril to form a stable ternary host-guest complex. Any guest pair that fits within the cavity of the cucurbituril may be employed. In some embodiments, the pair of guest molecules may form a charge transfer pair comprising an electron-rich and an electron-deficient compound. One of the first and second guest molecules acts as an electron acceptor and the other as an electron donor in the CT pair. For example, the first guest molecule may be an electron deficient molecule which acts an electron acceptor and the second guest molecule may be an electron rich molecule which acts as an electron donor or vice versa. In one embodiment, the cucurbituril is CB[8].

Suitable electron acceptors include 4,4'-bipyridinium derivatives, for example N,N'-dimethyldipyridyliumylethylene, and other related acceptors, such as those based on diazapyrenes and diazaphenanthrenes. Viologen compounds including alkyl viologens are particularly suitable for use in the present invention. Examples of alkyl viologen compounds include N,N'-dimethyl-4,4'-bipyridinium salts (also known as Paraquat).

Suitable electron donors include electron-rich aromatic molecules, for example 1,2-dihydroxybenzene, 1,3-dihydroxybenzene, 1,4-dihydroxybenzene, tetrathiafulvalene, naphthalenes such as 2,6-dihydroxynaphthalene and 2-naphthol, indoles and sesamol (3,4-methylenedioxyphenol). Polycyclic aromatic compounds in general may find use as suitable electron donors in the present invention. Examples of such compounds include anthracene and naphthacene.

Amino acids, such as tryptophan, tyrosine and phenylalanine may be suitable for use as electron donors. Peptide sequences comprising these amino acids at their terminus may be used. For example, a donor comprising an amino acid sequence N-WGG-C, N-GGW-C or N-GWG-C may be used.

In some embodiments, the guest molecules are a pair of compounds, where one of the pair is an A compound as set out in the table above (e.g. A1, A2, A3 etc.), and the other of the pair is a B compound as set out in the table above (e.g. B1, B2, B3 etc.).

Other suitable guest molecules include peptides such as WGG (Bush, M. E. et al *J. Am. Chem. Soc.* 2005, 127, 14511-14517).

An electron-rich guest molecule may be paired up with any electron-deficient CB[8] guest molecule. Examples of suitable pairs of guest molecules for use as described herein may include:

viologen and naphthol;
viologen and dihydroxybenzene;
viologen and tetrathiafulvalene;
viologen and indole;
N,N'-dimethyldipyridyliumylethylene and naphthol;
N,N'-dimethyldipyridyliumylethylene and dihydroxybenzene;
N,N'-dimethyldipyridyliumylethylene and tetrathiafulvalene;
N,N'-dimethyldipyridyliumylethylene and indole;
2,7-dimethyldiazapyrenium and naphthol;
2,7-dimethyldiazapyrenium and dihydroxybenzene;
2,7-dimethyldiazapyrenium and tetrathiafulvalene; and
2,7-dimethyldiazapyrenium and indole.

In particular, suitable pairs of guest molecules for use as described herein may include 2-naphthol and methyl viologen, 2,6-dihydroxynaphthalene and methyl viologen and tetrathiafulvalene and methyl viologen.

In one embodiment, the guest pair is a reference to a pair of guest molecules suitable for forming a ternary complex with CB[8].

In one embodiment, the guest molecule is preferably an ionic liquid. Typically, such guests are suitable for forming a complex with CB[7].

The ionic liquid typically comprises a cationic organic nitrogen heterocycle, which may be an aromatic nitrogen heterocycle (a heteroaryl) or a non aromatic nitrogen heterocycle. The ionic liquid also typically comprises a counter-anion to the cationic organic nitrogen heterocycle. The nitrogen heteroaryl group is preferably a nitrogen $C_{5-10}$heteroaryl group, most preferably a nitrogen $C_{5-6}$heteroaryl group, where the subscript refers to the total number of atoms in the ring or rings, including carbon and nitrogen atoms. The non aromatic nitrogen heterocycle is preferably a nitrogen $C_{5-6}$heterocycle, where the subscript refers to the total number of atoms in the ring or rings, including carbon and nitrogen atoms. A nitrogen atom in the ring of the nitrogen heterocycle is quaternised.

The counter-anion may be a halide, preferably a bromide. Other counter-anions suitable for use are those that result in a complex that is soluble in water.

The guest is preferably a compound, including a salt, comprising one of the following groups selected from the list consisting of: imidazolium moiety; pyridinium moiety; quinolinium moiety; pyrimidinium moiety; pyrrolium moiety; and quaternary pyrrolidine moiety.

Preferably, the guest comprises an imidazolium moiety. An especially preferred guest is 1-alkyl-3-alkylimidazolium, where the alkyl groups are optionally substituted.

1-Alkyl-3-alkylimidazolium compounds, where the alkyl groups are unsubstituted, are especially suitable for forming a complex with CB[7].

1-Alkyl-3-alkylimidazolium compounds, where the alkyl groups are unsubstituted, are especially suitable for forming a complex with CB[6]

1-Alkyl-3-alkylimidazolium compounds, where an alkyl group is substituted with aryl (preferably napthyl), are especially suitable for forming a complex with CB[8].

The 1-alkyl and 3-alkyl substituents may the same or different. Preferably, they are different.

In one embodiment, the 3-alkyl substituent is methyl, and is preferably unsubstituted.

In one embodiment, the 1-alkyl substituent is ethyl or butyl, and each is preferably unsubstituted.

In one embodiment, the optional substituent is aryl, preferably $C_{5-10}$aryl. Aryl includes carboaryl and heteroaryl. Aryl groups include phenyl, napthyl and quinolinyl.

In one embodiment, the alkyl groups described herein are linear alkyl groups.

Each alkyl group is independently a $C_{1-6}$alkyl group, preferably a $C_{1-4}$alkyl group.

The aryl substituent may itself be another 1-alkyl-3-substituted-imidazolium moiety (where the alkyl group is attached to the 3-position of the ring).

In another embodiment, the compound preferably comprises a pyridinium moiety.

The ionic liquid molecules describe above are particular useful for forming binary guest-host complexes. Complexes comprising two ionic liquid molecules as guests within a cucurbituril host are also encompassed by the present invention.

A cucurbituril may be capable of forming both binary and ternary complexes. For example, it has been previously noted that CB[6] compounds form ternary complexes with short chain 1-alkyl-3-methylimidazolium guest molecules, whilst longer chain 1-alkyl-3-methylimidazolium guest molecules form binary complexes with the cucurbituril host.

Preferred guests for use in the present invention are of the form $H^+X^-$, where $H^+$ is one of the following cations,

| Cation | Structure |
|---|---|
| A | 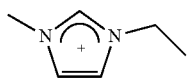 |
| B | 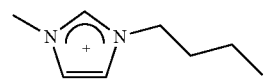 |
| C | 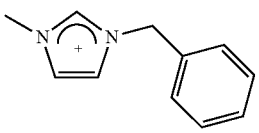 |
| D | 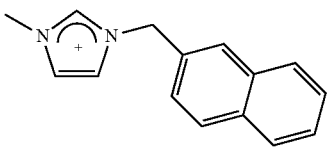 [SMILES: CN1C=CN(Cc2ccc3ccccc3c2)C1] |
| E | 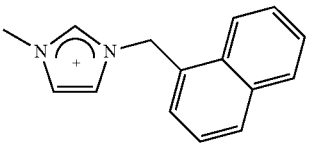 [SMILES: CN1C=CN(Cc2cccc3ccccc23)C1] |
| F | 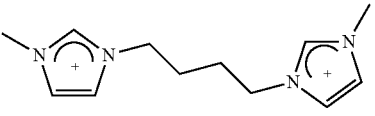 | and X⁻ is a suitable counter-anion, as defined above. A preferred counter anion is a halide anion, preferably Br⁻.

In a preferred embodiment, cation A or cation B may be used to form a complex with CB[7] or CB[6].

In a preferred embodiment, cation D or cation E may be used to form a complex with CB[8].

Cations A and B may be referred to as 1-ethyl-3-methylimidazolium and 1-butyl-3-methylimidazolium respectively.

Cations D and E may be referred to as 1-naphthalenylmethyl-3-methylimidazolium, where D is 1-naphthalen-2-ylmethyl-3-methylimidazolium and E is 1-naphthalen-1-ylmethyl-3-methylimidazolium.

Alternatively or additionally, the guest compounds may be an imidazolium salt of formula (I):

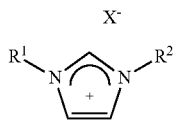

wherein X⁻ is a counter anion;
R¹ is independently selected from H and saturated $C_{1-6}$ alkyl;
R² is independently $C_{1-10}$ alkyl which may optionally contain one or more double or triple bonds, and may be optionally interrupted by a heteroatom selected from —O—, —S—, —NH—, and —B—, and may be optionally substituted.

In one embodiment, X⁻ is independently selected from the group consisting of Cl⁻, Br⁻, I⁻, $BF_4^-$, $PF_6^-$, OH⁻, SH⁻, $HSO_4^-$, $HCO_3^-$, $NTf_2$, $C_2N_5O_4$, $AlCl_4^-$, $Fe_3Cl_{12}$, $NO_3^-$, $NMeS_2^-$, $MeSO_3^-$, $SbF_6^-$, $PrCB_{11}H_{11}^-$, $AuCl_4^-$, $HF_2^-$, $NO_2^-$, $Ag(CN)_2^-$, and $NiCl_4^-$. In one embodiment, X⁻ is selected from Cl⁻, Br⁻, and I⁻.

In one embodiment, R¹ is selected from H and linear saturated $C_{1-6}$ alkyl.

In one embodiment, R² is linear $C_{1-10}$ alkyl, which may optionally contain one or more double bonds, and may be optionally interrupted by a heteroatom selected from —O—, —S—, —NH—, and —B—, and may be optionally substituted.

In one embodiment, R² is linear $C_{1-10}$ alkyl, which may optionally contain one or more double bonds, and may be optionally substituted.

In one embodiment, where a double or triple bond is present, it may be conjugated to the imidazolium moiety. Alternatively, the double or triple bond may not be conjugated to the imidazolium moiety.

In one embodiment, the optional substituents are independently selected from the group consisting of halo, optionally substituted $C_{5-20}$ aryl, —OR³, —OCOR³, =O, —SR³, =S, —BR³, —NR³R⁴, —NR³COR³, —N(R³)CONR³R⁴, —COOR³, —C(O)R³, —C(=O)SR³, —CONR³R⁴, —C(S)R³, —C(=S)SR³, and —C(=S)NR³R⁴,
where each of R³ and R⁴ is independently selected from H and optionally substituted saturated $C_{1-6}$ alkyl, $C_{5-20}$ aryl and $C_{1-6}$ alkylene-$C_{5-20}$ aryl.
or R³ and R⁴ may together may form an optionally saturated 5-, 6- or 7-membered heterocyclic ring which is optionally substituted with a group —R³.

In one embodiment, the optional substituents are independently selected from the group consisting of halo, optionally substituted $C_{5-20}$ aryl, —OR³, —OCOR³, —NR³R⁴, —NR³COR³, —N(R³)CONR³R⁴, —COOR³, —C(O)R³, and —CONR³R⁴, where R³ and R⁴ are defined as above.

Each $C_{5-20}$ aryl group may be independently selected from a $C_{6-20}$ carboaryl group or a $C_{5-20}$ heteroaryl group.

Examples of $C_{6-20}$ carboaryl groups include phenyl and napthyl.

Examples of $C_{5-20}$ heteroaryl groups include pyrrole (azole) ($C_5$), pyridine (azine) ($C_6$), furan (oxole) ($C_5$), thiophene (thiole) ($C_5$), oxazole ($C_5$), thiazole ($C_5$), imidazole (1,3-diazole) ($C_5$), pyrazole (1,2-diazole) ($C_5$), pyridazine (1,2-diazine) ($C_6$), and pyrimidine (1,3-diazine) ($C_6$) (e.g., cytosine, thymine, uracil).

Each $C_{5-20}$ aryl is preferably selected from optionally substituted phenyl, napthyl and imidazolium.

Each $C_{5-20}$ aryl group is optionally substituted. The optional substituents are independently selected from halo, $C_{1-6}$ alkyl, —OR³, —OCOR³, —NR³R⁴, —NR³COR³, —N(R³)CONR³R⁴, —COOR³, —C(O)R³, and —CONR³R⁴, where R³ and R⁴ are defined as above.

In one embodiment, each $C_{5-20}$ aryl group is optionally substituted with $C_{1-6}$ alkyl.

Where the $C_{5-20}$ aryl group is an imidazolium, such is preferably substituted at nitrogen with a group R¹ (thereby forming a quaternary nitrogen).

The compound of formula (I) comprises an imidazolium moiety having a substituent R² at the 1-position and a substituent R¹ at the 3-position. In a further aspect of the invention, the compound of formula (I) may be optionally further substituted at the 2-, 4- or 5-position with a group $R^A$, wherein $R^A$ has the same meaning as R¹.

The embodiments above are combinable in any combination, as appropriate.

Methods of Analysis

In one aspect of the invention there is provided a method for the detection of an analyte in a test sample using a construct where the linking compound is capable of binding the analyte.

The method relies on the formation of a construct providing an enhanced surface resonance effect. The formation of the construct occurs rapidly, and surface enhanced spectroscopic techniques may be used to probe the construct within minutes of the components of the construct, together with any analyte present, being contacted.

The method may comprise the steps of:
(i) providing a test sample to be tested for the presence of an analyte;
(ii) contacting the test sample with a linking compound, which compound is suitable for linking surfaces, wherein at least one of the surfaces is the surface of a nanoparticle, and each surface is suitable for providing a surface enhanced resonance effect, thereby to permit the linking compound to bind to analyte, where present;
(iii) subsequently providing a plurality of surfaces, and permitting the linking compound, optionally together with any analyte to which it is bound, to form a construct of linked surfaces, where the link is formed by a linker providing a constant inter-surface separation between the linked surfaces; and
(iv) analysing the formed construct by a surface enhanced spectroscopic technique, thereby to detect the presence of any analyte bound to the linking compound.

In the method above, the linking compound is exposed to the test sample prior to the incorporation of that linking compound into a construct. Thus, where any analyte is present in the test sample, the analyte is permitted to bind to the linking compound prior to the incorporation of the linking compound bound to the analyte into the construct.

The method may comprise the steps of:
(i) providing a test sample to be tested for the presence of an analyte;
(ii) contacting the test sample with a construct of linked surfaces, where the link is formed by a linker providing a constant inter-surface separation between the linked surfaces, wherein the linker comprises a linking compound, at least one of the surfaces is the surface of a nanoparticle, and each surface is suitable for providing a surface enhanced resonance effect;
(iii) permitting the linking compound to bind to analyte, where present; and
(iv) analysing the formed construct by a surface enhanced spectroscopic technique, thereby to detect the presence of any analyte bound to the linking compound.

In the method above, the formed construct is exposed to the test sample. Thus, where any analyte is present in the test sample, the analyte is permitted to bind to the linking compound, which is a component of the construct. In one embodiment, the analyte, where present, may bind directly to the linking compound. In one embodiment, the analyte may bind to the linking compound once the construct has at least in part disassembled, for example where the linking compound releases its connection to one or both surfaces. The released linking compound may then bind to analyte, where present, and then reform a link between surfaces.

The resulting formed construct may be analysed using the standard surface enhanced spectroscopic techniques described herein. SERS is particularly preferred.

In one embodiment, the surface enhanced spectroscopic technique is performed within 60 mins, within 30 mins, within 20 mins or within 10 mins of the time when the linking compound is first contacted with the test sample.

The amount of linking compound present in relation to nanoparticle may be varied, as appropriate, to control the growth of any assembly. In one embodiment, the linking compound is used in excess over the nanoparticle.

In one embodiment, the ratio of nanoparticle to linking compound is 1:X, where X is at least 10, at least 20, at least 30, at least 40, at least 50, at least 60, at least 80, at least 90, or at least 100. In one embodiment the ratio may refer to the molar ratio. In one embodiment the ratio may refer to the weight ratio.

Where a reaction limited assembly is preferred the value of X may be at most 60, at most 50, diffusion limited assembly is preferred the value of X may be at least 60, at least 70, at least 80, or at least 90.

The linking compound may be present at a concentration of at least 10, at least 100 or at least 1,000 nM (1 µM).

The linking compound may be present at a concentration of at most 1,000, at most 500, at most 200, at most 100, at most 50, at most 10, or at most 5 µM.

In one embodiment, the concentration of the linking compound is in a range where the minimum and maximum rates are selected from the embodiments above. For example, the concentration of the linking compound is in the range 1 to 5 µM.

The nanoparticle may be present at a concentration of at least 0.001 (1 µM), at least 0.01 (10 µM), at least 0.1, at least 1, at least 10, at least 100 or at least 1,000 nM (1 µM).

The nanoparticle may be present at a concentration of at most 1,000, at most 500, at most 200, at most 100, at most 50, or at most 10 µM.

In one embodiment, the concentration of the nanoparticle is in a range where the minimum and maximum rates are selected from the embodiments above. For example, the concentration of the nanoparticle is in the range 0.1 nM to 10 µM.

The form of the test sample is not particularly limited and it is dictated by the nature of the analyte, its source and possible purification and concentration. Typically, the test sample is an aqueous sample.

Where there is no change in the spectrum obtained by the surface enhanced spectroscopic technique after the exposure of the analyte to the construct materials, it may be determined that no binding has occurred. Thus, there is no analyte in the test sample.

Where there is a change in the spectrum obtained by the surface enhanced spectroscopic technique after the exposure of the analyte to the construct materials, it may be determined that a binding event has occurred. Thus, there is analyte present in the test sample. The level of binding may be determined using standard spectroscopic analysis and reference.

The term change may be used to refer to a comparison made to a standard spectrum obtained from a construct that has no analyte bound to the linking compound. Alternatively the spectroscopic methods may not rely on a comparison to a reference spectrum. The spectrum recorded may contain signature peaks that are distinctive of the analyte, and are not to be associated with the linking compound. The wavenumber of a peak, or a collection of peaks, may itself be characteristic of the analyte under investigation.

In one embodiment, the analyte is exposed to the mixture prior to the formation of the link between the surfaces. Here, the analyte (or analytes) may bind to the linking compound prior to its association with one or both of the surfaces. Once bound, the linking molecule together with the analyte bound may then form the connection between the surfaces. Where the linking compound is a host, the analyte guest (or analyte guests) may be accommodated in the cavity of the host prior to the host forming the connection between the surfaces.

In one embodiment, the analyte is exposed to the mixture after the formation of the link between the surfaces. In this embodiment, the analyte (or analytes) may be capable of binding to the linking compound directly without any dissociation of the construct. In another embodiment, the construct may be required to dissociate in order to allow the analyte to bind to the linking molecule. Once bound, the linking molecule together with the analyte may then form the connection between the surfaces.

Surface Enhanced Spectroscopy

The present invention provides constructs that are suitable for use in the detection of an analyte. The construct provides a region between the surfaces which has enhanced resonance characteristics. Using surface enhanced spectroscopic techniques the presence of an analyte within this region may be detected.

The presence of the analyte may be determined by the presence of characteristic signals associated with that analyte within the surface enhanced vibrational or electronic spectroscopy spectrum. Furthermore, where the linking compound is active to the spectroscopic technique employed, the presence of the analyte may be determined by a change in the wavelength (wavenumber) or intensity of a peak associated with the linking compound.

In one embodiment, the surface enhanced spectroscopy is surface enhanced Raman spectroscopy (SERS).

In one embodiment, the surface enhanced spectroscopy is Coherent anti-Stokes Raman spectroscopy (CARS).

In one embodiment, the surface enhanced spectroscopy is photoluminescence spectroscopy.

In one embodiment, the surface enhanced spectroscopy is infrared spectroscopy.

Surface enhanced spectroscopic techniques are well known to those in the field, and suitable techniques are described in detail herein.

In one embodiment, the surface enhanced spectroscopy is surface enhanced Raman spectroscopy (SERS).

In one embodiment, the acquisition time is at least 1, at least 2 or at least 5 s.

In one embodiment, the acquisition time is at most 60, at most 30, at most 20 or at most 10 s.

In one embodiment, the incident laser light is at a wavelength of at least 350 nm, at least 400 nm, at least 450 nm or at least 500 nm.

In one embodiment, the incident laser light is at a wavelength of at most 800 nm, at most 750 nm, at most 700 nm or at most 650 nm.

In one embodiment, the incident laser light is at a wavelength of 633 or 788 nm.

The incident power may be at most 50 mW, at most, 30 mW, at most 20 mW or at most 10 mW.

Methods of Preparation

In one aspect of the invention there is provided a method for the preparation of a construct that comprises a molecule bound to a linking compound.

The method may comprise the steps of:
(i) providing a molecule;
(ii) contacting the molecule with a linking compound, which compound is suitable for linking surfaces, wherein at least one of the surfaces is the surface of a nanoparticle, and each surface is suitable for providing a surface enhanced resonance effect, thereby to permit the linking compound to bind to the molecule; and
(iii) subsequently providing a plurality of surfaces, and permitting the linking compound, together with the molecule to which it is bound, to form a construct of linked surfaces, where the link is formed by a linker providing a constant inter-surface separation between the linked surfaces.

In the method above, the linking compound is exposed to the molecule prior to the incorporation of that linking compound into a construct. Thus the molecule is permitted to bind to the linking compound prior to the incorporation of the linking compound bound to the molecule into the construct.

The method may comprise the steps of:
(i) providing a molecule;
(ii) contacting the molecule with a construct of linked surfaces, where the link is formed by a linker providing a constant inter-surface separation between the linked surfaces, wherein the linker comprises a linking compound, at least one of the surfaces is the surface of a nanoparticle, and each surface is suitable for providing a surface enhanced resonance effect; and
(iii) permitting the linking compound to bind to the molecule In the method above, the formed construct is exposed to the molecule. Thus, the molecule is permitted to bind to the linking compound, which is a component of the construct. In one embodiment, the molecule may bind directly to the linking compound. In one embodiment, the molecule may bind to the linking compound once the construct has at least in part disassembled, for example where the linking compound releases its connection to one or both surfaces. The released linking compound may then bind to molecule, and then reform a link between surfaces.

In one embodiment the method of reparation is conducted under aqueous conditions.

The amount of linking compound present in relation to nanoparticle may be varied, as appropriate, to control the growth of any assembly. In one embodiment, the linking compound is used in excess over the nanoparticle.

In one embodiment, the ratio of nanoparticle to linking compound is 1:X, where X is at least 10, at least 20, at least 30, at least 40, at least 50, at least 60, at least 80, at least 90, or at least 100. In one embodiment the ratio may refer to the molar ratio. In one embodiment the ratio may refer to the weight ratio.

Where a reaction limited assembly is preferred the value of X may be at most 60, at most 50, diffusion limited assembly is preferred the value of X may be at least 60, at least 70, at least 80, or at least 90.

The linking compound may be present at a concentration of at least 10, at least 100 or at least 1,000 nM (1 μM).

The linking compound may be present at a concentration of at most 1,000, at most 500, at most 200, at most 100, at most 50, at most 10, or at most 5 μM.

In one embodiment, the concentration of the linking compound is in a range where the minimum and maximum rates are selected from the embodiments above. For example, the concentration of the linking compound is in the range 1 to 5 μM.

The nanoparticle may be present at a concentration of at least 0.001 (1 μM), at least 0.01 (10 μM), at least 0.1, at least 1, at least 10, at least 100 or at least 1,000 nM (1 μM).

The nanoparticle may be present at a concentration of at most 1,000, at most 500, at most 200, at most 100, at most 50, or at most 10 μM.

In one embodiment, the concentration of the nanoparticle is in a range where the minimum and maximum rates are selected from the embodiments above. For example, the concentration of the nanoparticle is in the range 0.1 nM to 10 μM.

The molecule may be present at a concentration of at least 1, at least 10, at least 100 or at least 1,000 nM (1 μM).

The molecule may be present at a concentration of at most 1,000, at most 500, at most 200, at most 100, at most 50, or at most 10 μM.

In one embodiment, the concentration of the molecule is in a range where the minimum and maximum rates are selected from the embodiments above. For example, the concentration of the molecule is in the range 1 nM to 100 μM.

The growth of any assembly may be monitored by UV-vis. Changes in the optical extinction values of characteristic peaks over time provide may provide an indication as to the type and degree of aggregation. For example, such techniques may be suitable for determining whether the aggregation is substantially linear or clustered. The techniques may be used ion real time to detect the formation of the aggregation, and the reaction may be stopped at suitable point once the desired degree of aggregation is obtained.

The method may be conducted under aqueous conditions.

The product of the method may be analysed by microscopic techniques, including TEM. Also suitable are UV-vis measurements. Where the linking compound is active to surface enhanced spectroscopic techniques, the linking molecule may be used a reporter for the local environment in which it is located.

Use of Construct

The present inventors have recognised that a construct may find use an enhancer of surface resonant effects, which effects are suitable for exploitation in surface enhanced resonance spectroscopy. The ability of the construct to hold a molecule within a specific junction between surfaces may allow that In a further aspect of the invention there is provided the use of a construct as a binding partner for a molecule. The construct for use in the present invention comprises linked surfaces, where the link is formed by a linker providing a fixed inter-surface separation between the linked surfaces, wherein the linker is a linking compound, and at least one of the surfaces is the surface of a nanoparticle. The compound is suitable for interacting with the molecule.

The construct may be used to bind a molecule to the linking compound. The molecule may be a precursor molecule. The application of a stimulus, such as the application of light, to the area of the bound precursor molecule (the hotspot) can be used to effect a change in the precursor such that it is converted to another chemical form. The intensity of trapped light in between the surfaces vastly amplifies the rate at which the precursor molecule is converted (the reaction rate), and further the binding interaction to the linking compound constrains the product formed.

Construct Per Se

In a further aspect there is provided a construct comprising linked surfaces, where the link is formed by a linker providing a fixed inter-surface separation between the linked surfaces, wherein the linker is a linking compound, and at least one of the surfaces is the surface of a nanoparticle. The compound is suitable for interacting with the molecule.

In one embodiment, the construct comprises three or more nanoparticles.

In one embodiment, the linking compound is not CB[5].

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

Experimental—Raman and SERS Spectroscopy of Cucurbit[n]Urils

Presented here is a systematic study of cucurbit[n]urils using Raman spectroscopy. Also reported is the SERS of CB[n]s while showing ppb (parts per billion) level detection capability and the ability to decipher mixtures. CB[n] homologues are studied by Raman and SERS spectroscopy and systematic trends are obtained which provide evidence of the changes in the ring strain with increasing ring size. The experimentally observed peaks are assigned by carrying out molecular simulations. Furthermore, the utility of SERS for studying CB[n]s on a surface-enhancing substrate such as Klarite™ is demonstrated and its detection when conjugated directly to gold nanoparticles; paving the way for SERS-based sensitive molecular recognition and detection assays with the latter particularly promising for real-time monitoring of CB[n] supramolecular complexes in solution.

Materials

Gold(III) chloride trihydrate and sodium borohydride were purchased from Sigma Aldrich and Alfa Aesar, respectively, and were used as received.

Synthesis of Cucurbit[n]Urils and Gold Nanoparticle-Capped Cucurbit[n]Urils

Synthesis of cucurbit[n]uril was carried out according to the reported procedure by Kim et al (Kim et al. *J. Am. Chem. Soc.* 2000, 122, 540). Isolation and purification were performed according to methods reported by some of the present inventors (Jiao et al. *Chem. Commun.* 2010, 46, 2007). Synthesis of gold nanoparticle-capped cucurbit[n]uril composites was done according to methods reported by some of the present inventors (Lee et al. *Chem. Commun.* 2010, 46, 2438).

The size of the different nanoparticle conjugates used in the paper for SERS were characterized with TEM. The mean sizes and standard deviation are given in Table 1 below.

TABLE 1

| Mean size of CB[n] gold nanoparticle conjugates | |
|---|---|
| Sample | Mean size ± standard deviation/nm |
| CB[5]-AuNPs | 3.6 ± 1.0 |
| CB[6]-AuNPs | 8.5 ± 2.6 |
| CB[7]-AuNPs | 3.5 ± 1.1 |

Raman/SERS

A Renishaw Raman InVia Microscope was employed. The Raman and SERS spectra on Klaritet surfaces were acquired with a single scan of 10 s each using a 785 nm laser at 2.8 mW incident power on the sample. Klaritet surfaces used in this work have a strong plasmonic resonance at 785 nm and hence are ideal for SERS measurements with the above laser. The SERS spectra on Klarite™ were recorded by placing 1 mM solution of the respective CB[n] in 20% DCl/$D_2O$ and glass cover slip was placed on top. In DCl/$D_2O$ all CB[n]s are soluble ensuring that the spectra are acquired under similar conditions. The SERS spectra for the conjugated nanoparticles were acquired with a 514 nm laser at an incident power of 1.1 mW with 3 accumulations of 30 s each. A 1200 g grating was employed to give a spectral resolution of approx. 4 $cm^{-1}$. For recording the SERS spectra a drop of 50 ml of approx. 0.1 mM CB[n]-gold nanoparticle conjugate solution in aqueous ethanol was dried on a glass slide.

Simulations with Spartan '08

The starting geometry for CB[5], CB[6] and CB[8] was retrieved from the CSD database (cucurbit[5]uril tetrahydrate clathrate, refcode: LIRTEL, cucurbit[6]uril refcode: BEBDOP and cucurbit[8]uril refcode: REDMET) and subsequently geometry-optimized at Hartree-Fock (3-21G basis set) level of theory. For CB[7], the geometry was built invoking standard bond lengths and bond angles using Spartan Model Builder followed by step-wise geometry optimizations on PM3 and HF/3-21G. Upon geometry optimization $D_{5h}$ symmetry was reached for CB[5] whereas CB[6]-CB[8] optimized structures were of $C_{2h}$ symmetry. Vibrational modes and Raman intensities were calculated using Spartan's inbuilt algorithms whereby the symmetry option was disabled as D5h symmetry for CB[5] has not been observed experimentally and thermal fluctuations are likely to cause distorted ground state geometries at ambient temperatures. A scaling factor of 0.90 was applied to correct the calculated vibrational frequencies as obtained with HF/3-21G for standard organic molecules (Scott *J. Phys. Chem.* 1996, 100, 16502).

SERS Spectra of CB[n] on Klarite

SERS spectra were recorded using CB[n] solutions in 20% DCl in $D_2O$ on Klarite™. Only 1 μL of their 1 mM solutions was placed on the SERS surface with a quartz cover glass on top. The spectrum of each of the CB[n] was easily recorded within 10 s at modest laser powers.

Results

Cucurbit[n]urils, where n=5-8, were synthesized and purified according to published methods (Jiao et al. *Chem. Commun.* 2010, 46, 2007; Kim et al. *J. Am. Chem. Soc.* 2000, 122, 540). The dry powder of each CB[n] was subjected to Raman investigation. The Stokes-shifted Raman spectra of all the homologues are presented in FIG. 1. The finger print region (400 $cm^{-1}$ to 2000 $cm^{-1}$) in the Raman spectra shows clear and identifiable peaks for each CB[n]. The spectra compare well with the single Raman spectrum of CB[5] published by Corma et al., in which neither the conditions nor any assignment have been reported (Corma et al. *Tetrahedron Lett.* 2007, 48, 4613). Nevertheless, upon closer examination of the spectra of the homologues, it is seen that the peaks either increase or decrease in frequency with the number (n) of glycouril units of the CB[n]. In particular, the two most intense peaks in the spectra, at approx. 830 $cm^{-1}$ and approx. 450 $cm^{-1}$ blue and red shift, respectively, with an increase in ring size (FIG. 1b). The 450 $cm^{-1}$ peak shifts negatively by 4 $cm^{-1}$ and the 830 $cm^{-1}$ peak shifts positively by 1-2 $cm^{-1}$ per additional glycouril unit. The 883 $cm^1$ peak shifts much more significantly by +8 $cm^1$ per additional glycouril unit. This amounts to a destabilization and stabilization, respectively, of −0.50 meV (450 $cm^{-1}$), +0.25 meV (830 $cm^{-1}$) and +1 meV (883 $cm^{-1}$). The other peaks seen in FIG. 1a do not shift significantly and hence have not been considered in the analysis below.

Computational simulation was carried out with Spartan '08 to visualize the Raman active vibrations in CB[n=5-7] and compare frequencies with experimental results (Spartan 08 is available from Wavefunction, Inc., 18401 Von Karman Avenue, Suite 370, Irvine, Calif. 92612; www.wavefun.com). Qualitative correlation of peak positions could be obtained only when the symmetry of the molecule was disregarded in the calculations, pointing to the inherent asymmetry in the actual structure as confirmed in the reported X-ray crystal structures (Kim et al. *J. Am. Chem. Soc.* 2000, 122, 540). The peak assignments and frequencies for CB[5] and CB[7] are listed in Table 2.

The difference in the calculated and observed frequencies, even after correcting by a factor of 0.9 (usually employed in such HF calculations) is due to the small basis set (split-valence 3-21G) employed in the calculations (Scott et al. *J. Phys. Chem.* 1996, 100, 16502). HF/3-21G calculations on standard organic molecules are known to systematically overestimate bond strengths but reproduce the experimental trends and systematic changes for molecules with similar electronic environments. Nevertheless, the correlation with experimental results is good.

Figure 2:
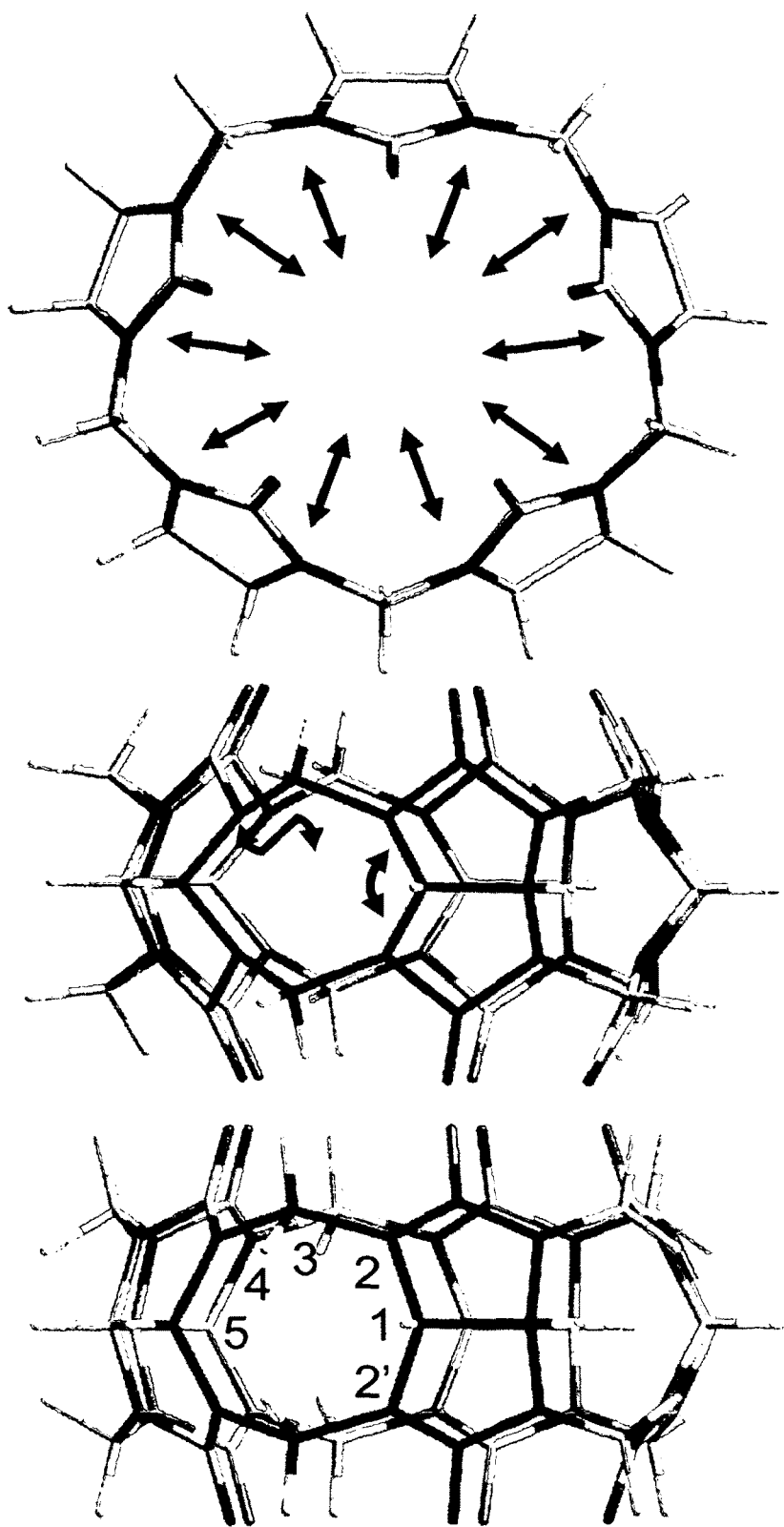
FIG. 2 is a pictorial representation of CB[5] vibrations for the 881 $cm^{-1}$ peak in (a) plan view depicting the overall ring breathing effect and in (b) side views showing the effect on the 8- and 5(glycouril)-membered ring as a result of the bending and twisting motions across N—C—N (2-1-20) and N—C—C—N (2-3-4-5) bonds. The vibration snapshots have been obtained with Spartan '08.

The 450 $cm^{-1}$ is a 'ring' scissor mode (in-phase 'scissor' vibration along the N—C—N bonds of the 5-membered glycouril ring), the peak at 830 $cm^{-1}$ is assigned to ring deformation modes (8-membered ring deforms out-of-phase with the 5-membered glycouril ring) while the 880 $cm^{-1}$ is a complex ring breathing like mode (FIG. 2) comprising of deforming and twisting motions. The simulations confirm the observations (FIG. 1) regarding peaks shifts with an increase in size of the cucurbit[n]urils studied here and this is discussed below.

TABLE 2

Raman frequencies and their assignments for CB[5] and CB[7]

| CB[5] | | CB[7] | | |
|---|---|---|---|---|
| Observed | Calculated[a] | Observed | Calculated[a] | Assignment[a,b] |
| 452 | 458 | 441 | 440 | σN—C—N |
| 655 | 644 | 655 | 646 | τHC—CH |
| 826 | 830 | 829 | 833 | δC—N—C + ρ$CH_2$ |
| 881 | 886 | 899 | 902 | βC—N—C + τN—C—C—N + νC—C |
| 1378 | 1360 | 1378 | 1361 | Symmetric νC—N |
| 1419 | 1417 | 1421 | 1420 | Asymmetric νC—N |
| 1745 | 1746 | 1745 | 1746 | νC=O |

[a]Based on Spartan '08 Hartree-Fock (3-21G) simulations.
[b]ν = stretch, β = bend, δ = deformation, ρ = rock, σ = scissor and τ = twist.

Raman frequencies can be modelled using the harmonic oscillator:

$$\vec{v} \propto \sqrt{k/\mu}$$

where the frequency will depend not only on the force constant (k) but also on the reduced mass (μ) of the atoms involved in the vibration. For cases involving the same atoms in different molecules, an increase in stretching frequencies can directly be inferred as an increase in bond stiffness. However, this simplistic analysis is not directly valid for deformations, scissors or twists present in macrocyclic ring structures such as cucubit[n]urils in which steric factors and bond angle strains can alter the overall stability/energy of the structure and therefore affect the vibrational frequency of a given mode.

Understanding these could be critical for deciphering differences in stability and reactivity of homologous cucurbiturils. Interestingly peaks (Table 1) associated with deformations, bends or twists increase or decrease in frequency with the CB[n] size. The simple stretches are mostly unaffected. This observation clearly implicates steric and ring strain factors for the observed systematic variation. The observed slight increase in frequency for the 830 $cm^{-1}$ band with increasing size of the CB[n] is probably a result of increase in strain due to an increase in the regular $sp^3$ bond angle. However, for the 880 $cm^{-1}$ vibration, additional repulsion between the N—CH—N and —CH2 hydrogen atoms occurs, which are probably driven closer with an increase in the molecular size, resulting in a larger increase in frequency with an increase in macromolecular size. For the 450 $cm^{-1}$ vibration the effect is opposite because it is a scissoring vibration involving the N—C—N bonds (the 5-membered glycoruril rings bend towards each other) and therefore becomes less strained with an increase in ring size.

Figure 5:
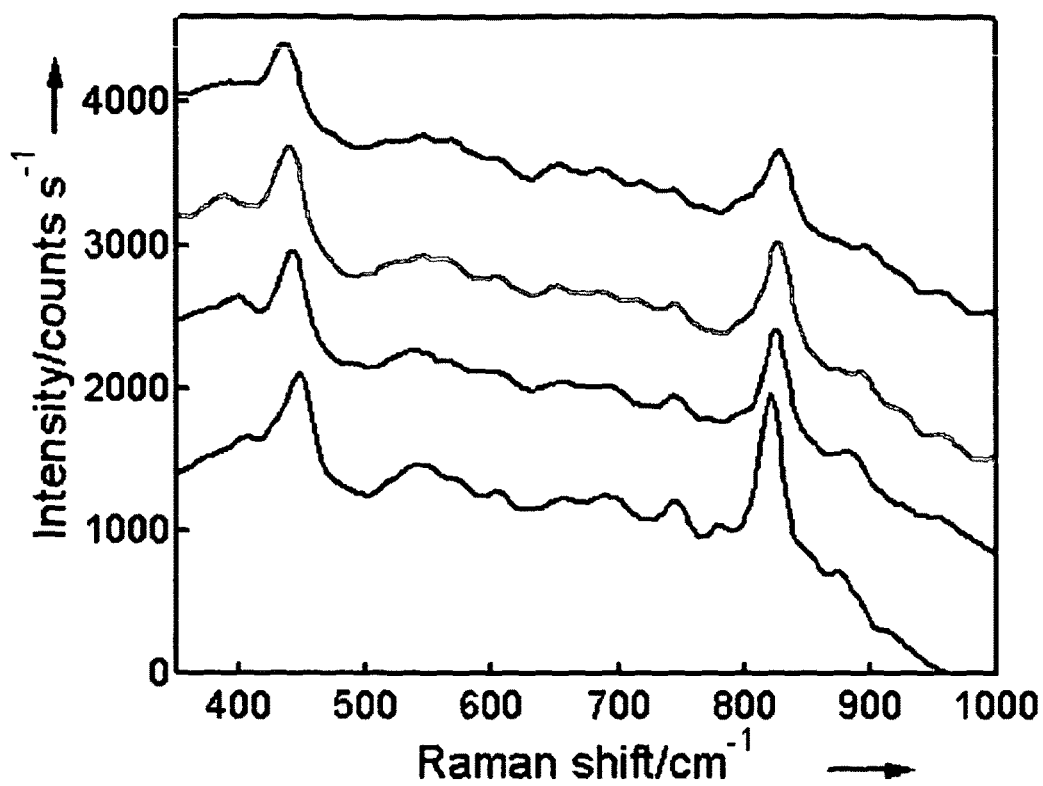
FIG. 5 is SERS spectra of CB[n] solutions recorded on Klarite™. The spectra are from bottom to top CB[5], CB[6], CB[7] and CB[8]. Acquisition conditions: 785 nm excitation, single 10 s scan, laser power: 2.8 mW.

Thus, Raman spectroscopy can be used for characterizing cucurbit[n]urils and identifying them in bulk samples. For trace level or surface based analysis, however, the SERS effect needs to be utilized. Here the surface-enhancement of Klarite™ nanostructured surfaces is employed to obtain SERS spectra of the CB[n] (see FIG. 5). The trend in the shift of the 830 $cm^{-1}$ and the 450 $cm^{-1}$ peaks with increasing size (n) of the CB[n] is evident in the SERS spectra as well. It is noted that the SERS peaks are broader than their Raman counterparts, possibly due to weak interaction of molecular orbitals with the metal surface in the solution since CB[n] adsorbs on gold through interaction of their carbonyl groups with the metal surface (An et al. *Chem. Commun.* 2008, 1989). With SERS detection it was possible to detect CB[5] even at the 10 ppb level in an aqueous solution.

Furthermore, the SERS effect is highly localized near surfaces and decays exponentially with increasing distance from a surface. Therefore, only those molecules which are on or near the SERS surface experience the enhancement effect. Thus, even after washing the excess solutions off the Klarite surface, the SERS spectra of the physisorbed CB[n] could be recorded with the peak intensities showing only a slight decrease of about 10%. It is noted that the SERS spectra show fewer peaks compared to the Raman spectra. This could be due to the imposition of additional surface selection rules in SERS. Moreover, CB[5] shows higher intensities of peaks than others indicating stronger adsorption on the surface and also slightly higher surface coverage due to its smaller size. We also observe that the SERS peaks are broader than their Raman counterparts, possibly due to weak interaction of molecular orbitals with the metal surface in the solution.

Figure 3:
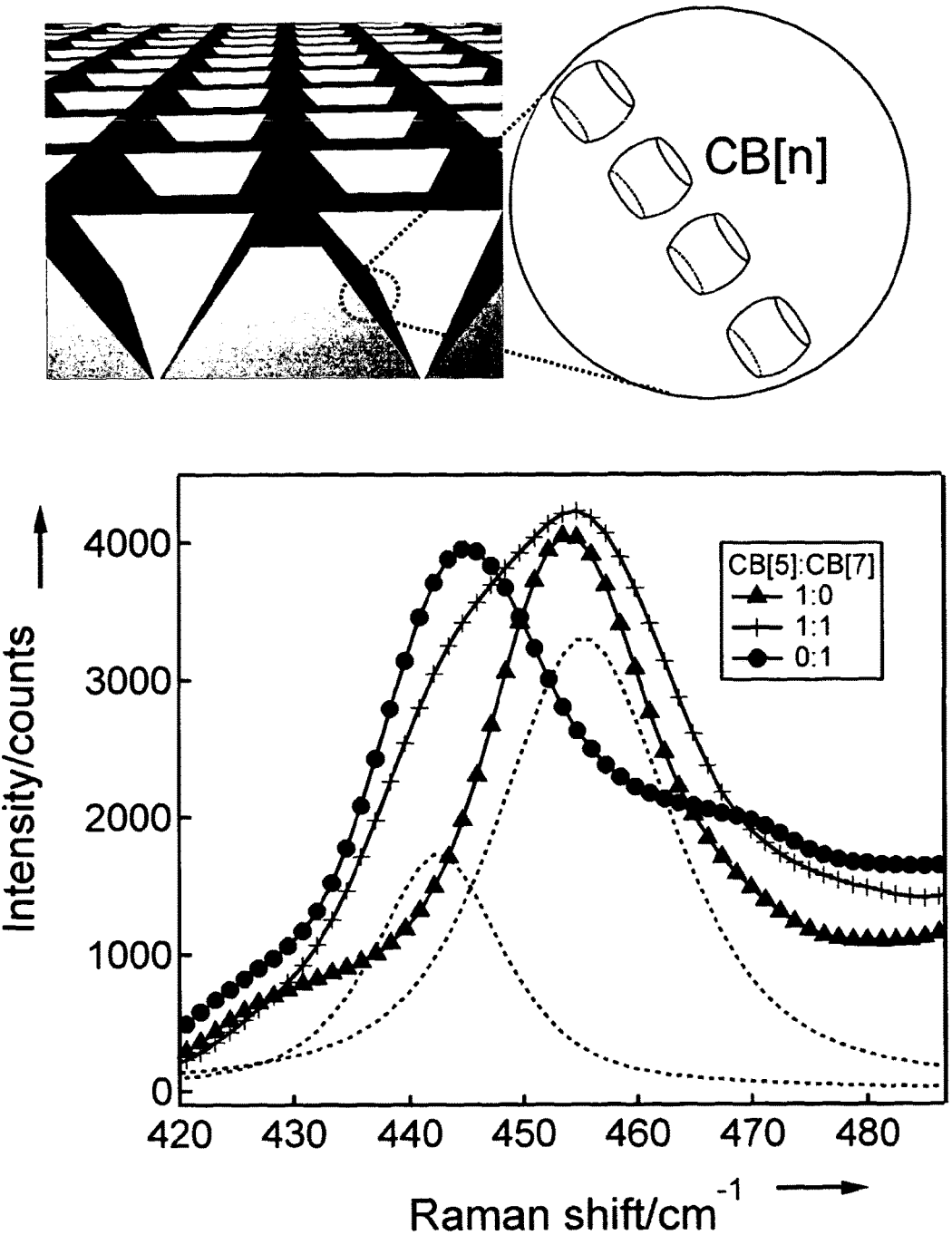
FIG. 3 (a) is a schematic of CB[n] on Klarite™ nanostructured surface. (b) is a SERS spectra of 1 mM CB[n] solutions recorded on Klarite™. The deconvolved peaks (dotted) show the individual CB[5] and CB[7] components in the spectrum of the mixture (at approx. 455 $cm^{-1}$ from most intense peak is 1:1, then 1:0, then 0:1 [5]:[7]). Acquisition conditions: 785 nm excitation, single 10 s scan.
Figure 6:
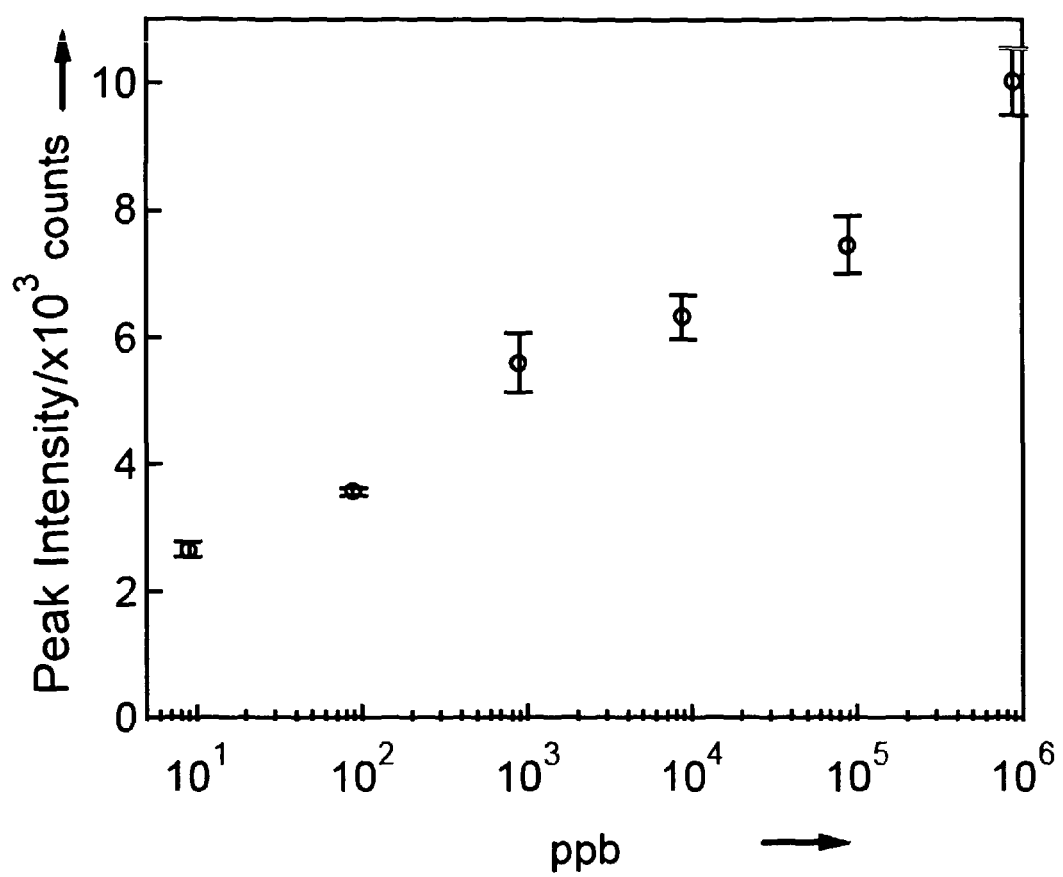
FIG. 6 shows the relationship of SERS peak intensity with concentration. The SERS spectra were recorded on Klarite™ using 1 µL of each concentration. The solutions were prepared by serial dilution of 1 mM stock solution. Acquisition conditions: 785 nm excitation, laser power: 2.8 mW.

The SERS peak intensities were found to increase with concentration (see FIG. 6). Furthermore, owing to the systematic shifts observed in the Raman peaks as a function of macromolecular size, the spectra remain distinguishable and allow for mixtures of CB[n]s to be analyzed. For example, CB[5] and CB[7] could be identified in a mixture of their aqueous solutions with SERS by deconvoluting the peak around 450 cm$^{-1}$. The spectra are presented in FIG. 3. FIG. 6 shows the dependence of the 450 cm$^{-1}$ peak intensity with concentration. A 10 ppb level of CB[5] could be easily detected with SERS. A log dependence of the intensity of the CB[n] peaks is probably due to kinetics of the adsorption process. In the study by An et al., monolayers of CB[n] were formed on a gold surface by overnight soaking, however, here the process was undertaken over a few minutes.

It is pertinent to point out that during the synthesis of cucurbit[n]urils CB[5] and CB[7] are extracted as one fraction and CB[6] and CB[8] are separated as the second fraction, before further purification into individual components from their binary mixtures. Hence this result is significant as it presents a way of in situ analysis of the binary mixtures and monitoring the efficiency of purification procedure during the synthesis process. It is worth pointing out that the SERS analysis was done only with a single 10 s scan.

Figure 4:
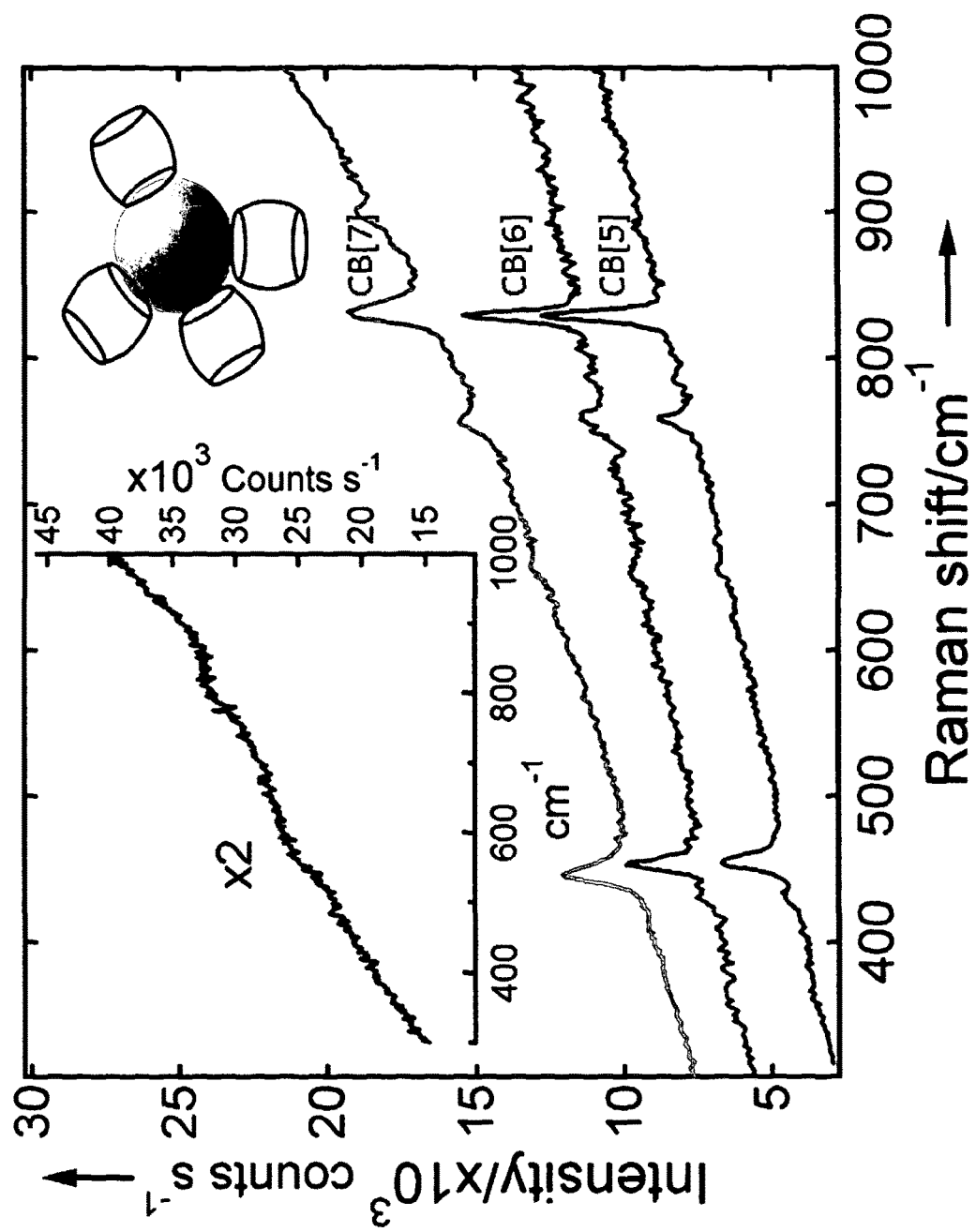
FIG. 4 is a SERS of CB[n=5-7] conjugated to gold nanoparticles (CB[5] (bottom), CB[6] (middle), CB[7] (top)). The left inset is the control spectrum (×2) recorded on Au nanoparticles not conjugated to CB[n]s. Acquisition conditions: 514 nm excitation, 30 s scan, 3 accumulations. Spectra are offset for clarity.

Gold nanoparticles can also act as SERS transducers in solution. Some of the present inventors have recently synthesised cucurbit[n]urils capped by gold nanoparticles (Lee *Chem. Commun.* 2010, 46, 2438). These nanoparticle conjugates present an attractive option for carrying out in situ SERS analysis directly in aqueous media. Presented here are data on the SERS of CB[n=5-7] capped with gold nanoparticles in FIG. 4. The SERS spectra are obtained with a 514 nm laser tuned to excite the localized plasmons of gold nanoparticles causing the enhancement of the signals. Clear and unambiguous SERS peaks of CB[n]s conjugated to gold nanoparticles are seen. The inset in FIG. 4 shows the control spectrum of gold nanoparticles alone (without CB[n]s). Acquisition of in situ SERS spectra could prove immensely useful for deciphering binding mechanisms, real-time reaction monitoring and for developing applications in sensing with CB[n]s acting as selective hosts permitting the detection of analyte (guest) peaks.

Described above is a detailed study of all the major homologues of cucurbit[n]urils using Raman and SERS. Systematic shifts of the peaks are observed with increasing size of the CB[n]s. The observed trend is consistent in both Raman and SERS spectra. With the aid of computational simulation, peaks have been assigned to their corresponding vibrational modes, providing a further rationalization of the observed spectra, as well as the shifts in vibrational frequencies. These shifts relate to changes in steric factors and bond angle strains with the size of CB[n]s which might help comprehend changes in their reactivity. Furthermore SERS has become an increasingly accurate and convenient way of characterization as well as identification at an ultra-sensitive level. Employing SERS the characterization of CB[n]s is demonstrated, as well as detection at an ultrasensitive level of 10 ppb and differentiation in mixtures of CB[n]s, all of which will be highly advantageous in purification and isolation procedures as well in sensors. The work above establishes the use of Raman and SERS for the characterization and identification of CB[n]s. It is also a significant step towards realizing ultrasensitive molecular-recognition assays using SERS especially for aqueous chemical and supramolecular systems.

Experimental—Plasmonic Junctions

CB Synthesis

Synthesis of cucurbit[5]uril was carried out according to the reported procedure by Kim et al. 62 Isolation and purification were performed according to methods reported earlier. 37 To observe the effect of the concentration of CB[5] upon the aggregation of the Au nanospheres (diameter 20 nm), 63 an aqueous solution of 2.4 mM CB[5] was made. The solution was diluted 100-fold and 10-20 µL added to 2 mL of the as-supplied AuNPs, initiating aggregation. The initial AuNP:CB[5] solution was stirred gently for ca. 10 s with a magnetic bar to aid thorough mixing. Inspection of the AuNP:CB[5] solution revealed a colour change from ruby red to purple, indicative of the coagulation of Au colloids.

Extinction Measurements

A polystyrene cuvette, path length 10 mm, was used to contain the AuNP:CB[5] solution while illuminating with a focused 400-1000 nm tungsten halogen light source (Ocean Optics, LS-1). The transmitted light was collected and sampled with a TE-cooled spectrometer (Ocean Optics, QE 65000) using custom-written software allowing for time-resolved spectroscopy.

Electron Microscopy

Transmission electron microscopy (TEM) was carried out on a JEOL 2000FX TEM under an accelerating voltage of 200 kV. Samples were prepared by applying one drop of the reaction mixture containing AuNP:CB[5] at different elapsed times onto a holey carbon coated copper TEM grid (400 mesh).

SERS Measurements

SERS measurements were performed on a Renishaw InVia Raman confocal microscope with a 5×(NA=0.12) objective in the backscattering geometry. The spectral acquisition time was 10 s with a 1200 lines mm$^{-1}$ grating, giving a resolution of 4 cm$^{-1}$. The solution was excited with the 633 and 785 nm laser lines from HeNe and solid-state lasers, respectively. All measurements were performed at room temperature and were calibrated with respect to Si. Both the time-resolved Raman and extinction measurements were performed simultaneously on each aggregating solution.

Results

The rich host-guest chemistry of cucurbit[n]urils along with their rigid geometry and ability to bind to gold makes them a prime candidate for mediating aggregation of nanoparticles to form accessible hot spots for use in SERS. In order to understand the effect of CB[5] on the plasmonics of aggregation, we studied the resulting change in optical extinction, in a time-resolved manner, as a function of CB[5] concentration. This modifies the CB surface coverage on the AuNPs (always here extremely sparse), which determines the likelihood of a collision resulting in coagulation between two CB-capped AuNPs and hence the rate of global aggregation. While the detailed results we report here are for 20 nm AuNPs, similar results are seen for diameters from 10 to 100 nm AuNPs.

Time-Resolved Extinction of AuNP:CB[5] Assemblies

Figure 8:
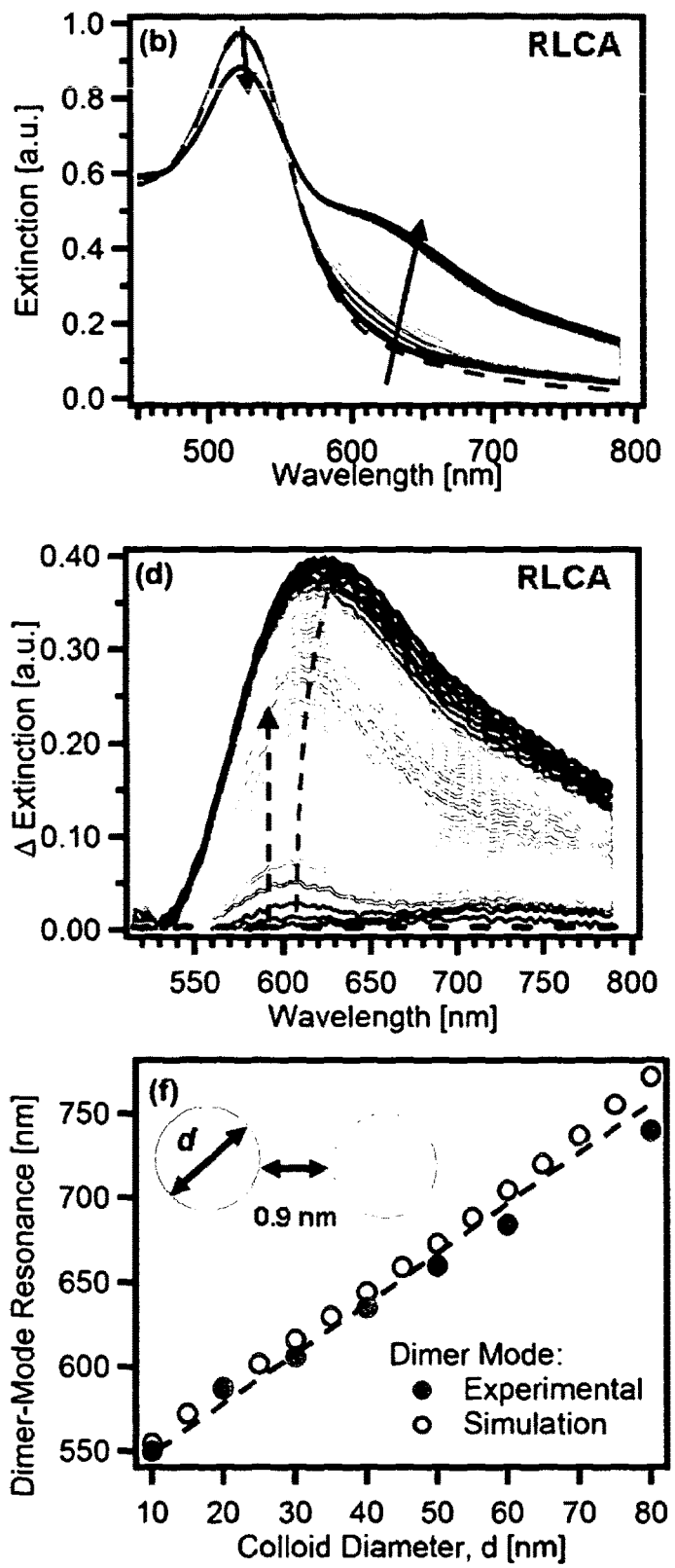
FIGS. 8 (a) and (b) are time-resolved extinction spectra of aggregating AuNP:CB[5] samples for (a) DLCA (1:80) and (b) RLCA (1:60) kinetics (arrows guide the eye). Spectra acquired at 1 min intervals for 2 h. (c,d) Difference spectra obtained from (a,b) by removing the isolated single AuNP contributions. Extinction difference fits best to sum of two Lorentzian modes (dashed) which grow with time. (e) Extracted intensity with time of dimer-like mode at 590 nm (blue, light-blue for DLCA, RLCA) and coupled chain mode (green, light-green for DLCA, RLCA). (f) Measured Plasmon resonance of CB[5]-coupled dimer-like mode as a function of AuNP diameter, with the theoretical simulations performed using the boundary element method 45 using the dielectric function for Au from Johnson and Christy.46 Simulations include size corrections and assumes a particle separation of 0.9 nm. The electric field is polarized parallel to the interparticle axis.

Time-resolved UV-vis spectra representative of the two main kinetic growth regimes at AuNP:CB[5] ratios of 1:80 and 1:60 are shown in FIGS. 8 (a) and (b). Higher CB[5] ratios correspond to diffusion-limited growth of the AuNPs since their sticking probability is high and collisions are more likely to result in successful coagulation. For low concentrations of CB[5], the aggregation is reaction-limited as fewer collisions result in aggregation. The sub-millisecond acquisition of the evolving spectra is continued over 2 h (progressing according to the arrows). Spectral features for both kinetic growth regimes are discussed below. However, it is apparent that the information is rather different from that provided by quasi-static light scattering, which under model assumptions gives the fractal dimension of the aggregates (Meakin Aggregation Kinetics. *Phys. Scr.* 1992, 46, 295) and dynamic light scattering which under further assumptions suggests the cluster anisotropy (Lin et al. Universal Reaction-Limited Colloid Aggregation. *Phys. Rev. A* 1990, 41, 2005; Lin et al. Universal Diffusion-Limited Aggregation. *J. Phys.: Condens. Matter* 1990, 2, 3093). The spectra instead here reveal the smallest-scale features of the aggregates from the coupling of particles.

Aggregation of the AuNPs in the DLCA regime (FIG. 8 (a)) shows extinction spectra which rapidly decrease and broaden the surface plasmon resonance (SPR) band of the AuNP at 525 nm (Maier *Plasmonics Fundamentals and Applications*; Springer: New York, 2007; p 162; Bohren et al. *Absorption and Scattering of Light by Small Particles*; Wiley-Interscience: New York, 1983; pp 75) as well as the appearance of a strong secondary broad band centered at 650 nm, arising from the aggregation. Over time, this aggregate band red shifts to a maximum of 690 nm. Aggregation proceeding in the RLCA regime (1:60, FIG. 8 (b)) over 2 h follows a similar but much slower growth curve corresponding to the first 2 min of the 1:80 AuNP:CB[5] aggregate. Notably, similar plasmonic properties are achieved through different growth routes, which are due to the reproducible nature of the interparticle mediation.

To isolate the 600-700 nm aggregate plasmon band in greater detail, the difference spectra of FIGS. 8 (a) and (b) are obtained by subtracting proportionate amounts of the single AuNP spectra to give FIGS. 8 (c) and (d). Decomposition of the broad aggregate band for both the DLCA and RLCA spectra reveals a superposition of two distinct modes centered at 590 and approx. 650 nm. Fitting to two Lorenztian functions supports this observation and shows that the mode at 590 nm remains stationary in position while the second mode around 650 nm red shifts during aggregation (arrows track the peak). In the case of DLCA, the initial aggregate mode grows rapidly and begins to saturate when the 590 nm mode saturates in intensity (FIG. 8 (e)). Subsequently, the resonance at 650 nm then rapidly red shifts, while the mode at 590 nm remains fixed in position. This change in spectral behaviour is believed to correspond to a change in the dominant growth mechanism in solution, from the rapid formation of dimers and short chains to the growth of larger size aggregates following the constant DLCA reaction kernel (Lin et al. Universal Diffusion-Limited Aggregation. *J. Phys.: Condens. Matter* 1990, 2, 3093). Time resolving the evolving aggregate through TEM micrographs elucidates the topological origins of the extinction spectra for both kinetic regimes.

Relating Topology with Optical Properties

Figure 9:
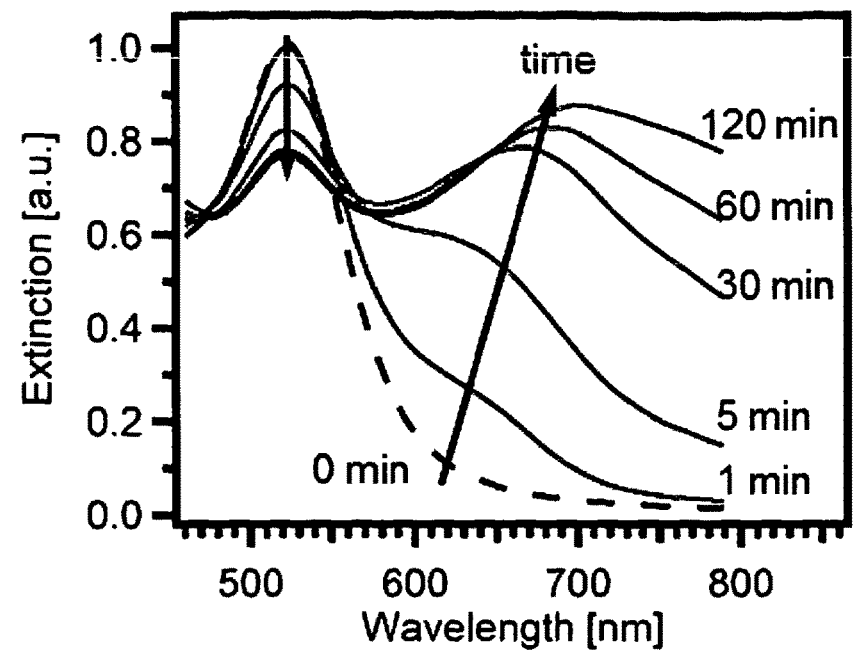
FIGS. 9 (a) and (b) are optical extinction spectra of 1:80 (a) and 1:60 (b) AuNP:CB[5] solutions with increasing time. TEM images from typical aggregation products formed at the indicated time elapsed. Differences in topology correspond to DLCA (a) and RLCA (b) regimes.
Figure 9:
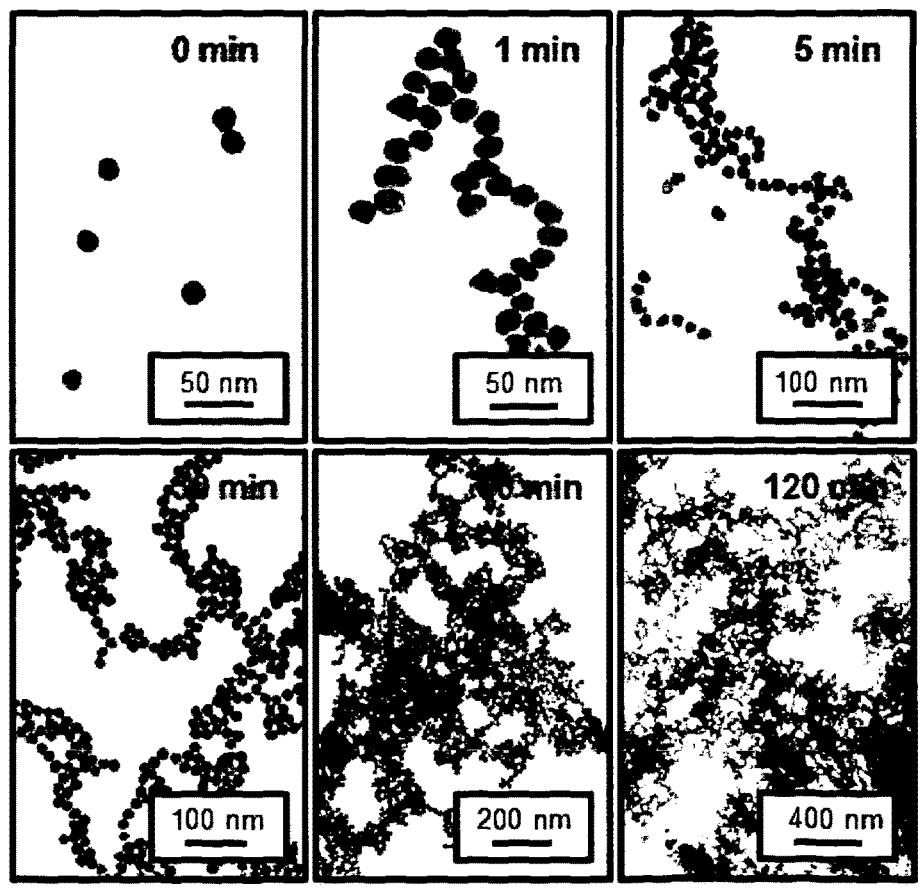
Figure 9:
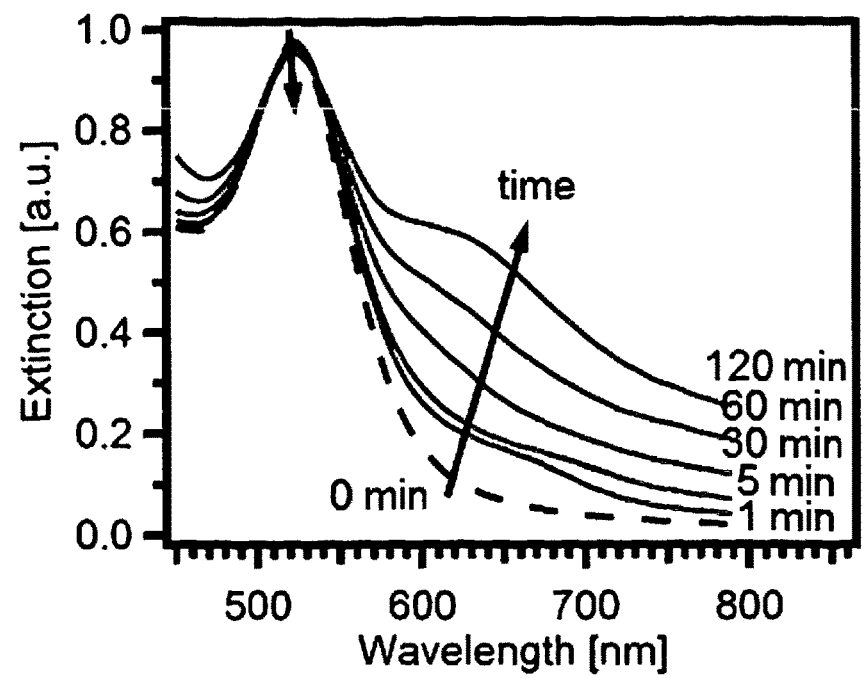
Figure 9:
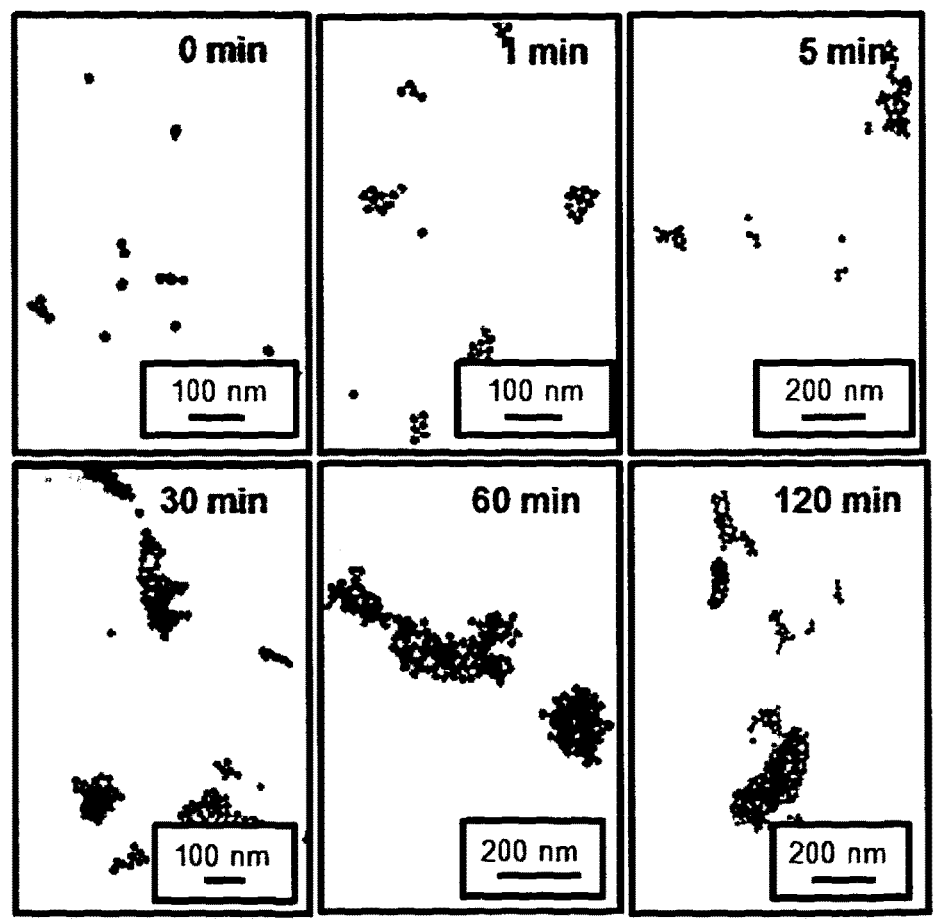

Insight into the size and topology of the grown AuNP: CB[5] aggregates is provided by TEM images obtained from aliquots extracted from the AuNP:CB[5] 1:80 and 1:60 aggregating solution at different points in time. The samples are dried immediately onto holey carbon grids (FIGS. 9 (a) and (b)). By measuring the optical extinction in solution during growth, comparisons can be made between the far-field optics and local aggregate structure.

Figure 16:
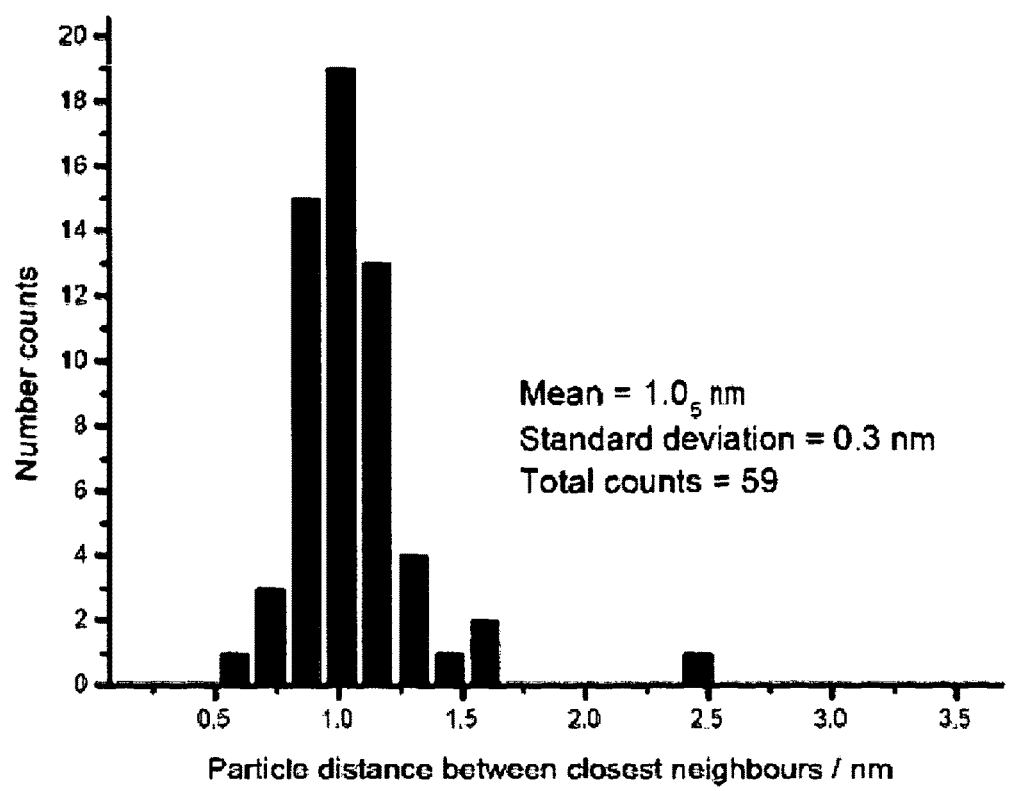
FIG. 16 shows the distribution of CB[5] mediated spacing between gold nanoparticles. The figure is a histogram of the average CB[5]-mediated AuNP spacing from the TEM image acquired at t=1 min for the DLCA regime (AuNP:CB[5] is 1:80). Average spacing is that of the ca. 1 nm of the Cucurbit[n]uril portal-to-portal separation.

The TEM of 1:80 AuNP:CB[5] at 1 min reveals the formation of open, elongated chain-like structures. These are consistent with DLCA growth since the colliding particles are unable to reach the very center of growing clusters, instead colliding with higher probability with the outermost structures. Even after 30 min, the clusters remain sparse and open, while after 2 h, quasi-fractal networks on the micrometer-scale form, which is in agreement with the DLCA growth model. A different behaviour is apparent for 1:60 AuNP:CB[5] in which tight compact clusters form and slowly grow by RLCA. Throughout, the average particle spacing is approx. 0.9 nm as determined from analysis of TEM images (see FIG. 16). This clearly indicates that CB[5] is an effective mediator to bring about aggregation and successfully controls the gap size defined by the molecular geometry (as also shown by the distinct plasmonic modes).

Using these topological insights, we are able to explain the plasmonic evolution within the kinetic models. The subnanometer spacing within the aggregates introduces additional electromagnetic interactions between closely spaced AuNPs, resulting in a shift in their resonance wavelength that increases with the number and proximity of neighbouring AuNPs up to a saturation limit (Kreibig et al. *Optical Properties of Metal Clusters*; Toennies, J. P., Ed.; Springer: Berlin, 1995; p 23.; Myroshnychenko et al. *Chem. Soc. Rev.* 2008, 37, 1792; Ghosh et al. *Chem. Rev.* 2007, 107, 4797; Daniel et al. *Chem. Rev.* 2004, 104, 293; Alu et al. *Phys. Rev. B* 2006, 74, 2054361). The resonance mode at 590 nm is identified as the longitudinal plasmon resonance of a 20 nm particle dimer with a separation of −1 nm, in close agreement with our theoretical simulations and consistent with the TEM of CB[5]-mediated AuNP aggregates. This mode scales as theoretically expected with AuNP diameter (FIG. 8 (f)). After a short time, these dimers are embedded in larger clusters.

Figure 17:
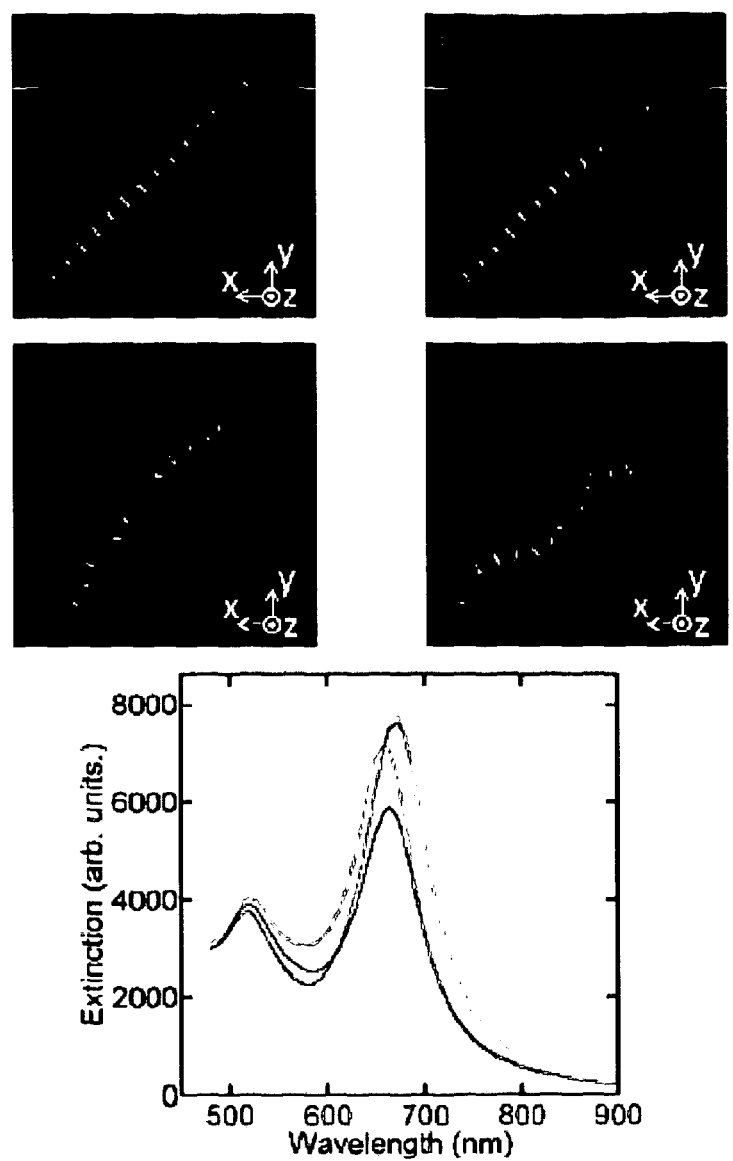
FIG. 17 shows simulations for the preparation of linear and kinked chains. The results shown have been obtained with plane wave illumination and were done in water to simulate the experimental conditions. Top: Simulations for linear and kinked chain showing the modulus of the electric field amplitude at resonant wavelength for straight ordered and progressively disordered chains of 20 nm diameter gold spheres in water separated by 0.9 nm. The illumination is a plane wave with propagation along 1x+1z direction, and the electric field is linearly polarized in the xz plane. Logarithmic colour scale is used, with bright and dark colours corresponding to electric field enhancements of 140 and 0.25 respectively. Bottom: Corresponding extinction spectra for the different configurations shown above. These calculations are performed using the multiple multipole method OpenMaX[3]. The extinction spectrum for a perfectly linear chain is similar in peak wavelength to that of irregular and kinked chains.

However, our simulations of kinked chains reveal that component dimers may be locally excited within larger disordered chain assemblies. The well-defined "dimer" mode thus arises from many precisely equivalent CB[5]-defined junctions. The broader mode at 650 nm is identified as a many-body coupled mode consistent with mutual coupling in the nanochains which progressively undergo resonance shifts with increasing numbers of appropriately illuminated constituent nanoparticles. Theory predicts an inherent saturation in interparticle coupling after approx. 10 NPs within nano-chains, leading to a saturation of the red shift, which is indeed seen experimentally for DLCA aggregates. Surprisingly, our simulations reveal that nonlinear disordered chains support modes similar to those of straight chains (see FIG. 17), implying that the model introduced here is robust to structural imperfections. The TEM images show DLCA aggregates to be composed of such chain-like structures, in agreement with the spectral identification of this chain mode. Finally, at long times, the formation of micrometer-sized aggregates at the visible λ scale are seen, and the extinction spectra show a rapidly growing near-infrared tail whose origin is currently poorly understood (Klar *Biosensing with Plasmonic Nanoparticles*. In Nanophotonics with Surface Plasmons; Shalaev, V. M., Kawata, S., Eds.; Elsevier: Amsterdam, 2007; pp 253; Quinten *J. Clust. Sci.* 1999, 10, 319; Norman et al. *J. Phys, Chem. B* 2002, 106, 7005; Liebsch et al. *J. Phys. C: Solid State* 1983, 16, 5375). We identify the mode still remaining near the isolated AuNP resonance at 525 nm as emerging from the transverse mode (with light polarized across the chains).

This precisely spaced CB[5]:AuNP system allows far-field interrogation of nanoscale growth with millisecond acquisition times. Existing techniques to probe aggregate growth such as dynamic and static light scattering are only able to reveal an ensemble-average hydrodynamic radius and fractal parameter; a measure of the large-scale aggregate topology over a much longer acquisition time. The data presented here reveal that in situ study of local growth is possible, with high sensitivity to nanoscale architecture. In addition to elucidation of local structure, the concentration of CB[5] has a profound effect on the growth rate and red shift of aggregate plasmon peaks under both reaction-limited and diffusion-limited aggregation regimes.

Plasmonics of Precise-Spaced Nanoparticle Assemblies

The kinetics of aggregation affects the plasmonic profile of the aggregate through the optically coupled topology. The kinetics may be parameterized from the far-field extinction by monitoring specific wavelengths, but this can be misleading. For example, previous reports have determined the kinetic rate by the decrease in the single nanoparticle SPR band (Moskovits et al. *J. Phys. Chem. B* 2005, 793 109, 14755) (which however is convoluted with the transverse mode of the chains) or by the peak aggregate wavelength (Aslan et al. *Anal. Chem.* 2005, 77, 2007; Dammer et al. *Phys. Chem. Chem. Phys* 2009, 11, 5455) (which is blurred if the gap separations are not precisely controlled). An improved approach is to measure the integrated extinction over the optically active spectral region from 590 to 700 nm (Aslan et al. *J. Phys. Chem. B* 2004, 108, 15631). Here we directly compare the spectral peak shifts in the instantaneous spectra with the integrated extinction, summing the extinction difference spectra from 590 to 700 nm. By increasing the CB[5] to AuNP ratio, the kinetic rates can be varied, altering the dominant topology of the aggregates with direct consequences on their use as SERS substrates. The effect of kinetics on the plasmonics of CB[5]-mediated aggregates is discussed below.

Comparing the integrated extinction as a function of time for various AuNP:CB[5] ratios (FIG. 4a) reveals the transition from RLCA to DLCA kinetics with increasing CB[5] concentration. This is consistent with the known growth in hydrodynamic radius, r, with time (Mohanty et al. *Angew. Chem.* 2005, 117, 3816) where the extinction is dominated by the $r^6$ optical scattering cross section in a quasi-static approach. For the RLCA regime, the low probability of sticking leads to a cluster capture cross section that increases with cluster size, effectively producing an autocatalytic reaction scheme (Norman et al. *J. Phys. Chem. B* 2002, 106, 7005). This is observed as a marked transition in the behaviour of the integrated extinction over the lifetime of the aggregation. The RLCA regime shows a linear increase in integrated extinction, while the DLCA displays a sudden change after approx. 10 min. For the DLCA regimes (1:>60), the aggregation rate appears to be a summation of two mechanisms: the immediate formation of NP dimers followed by subsequent chain-like multiparticle growth. However, our spectral dynamics reveal this to be a result of the complicated plasmonic origin of these Au nanocomposites. Both the extinction strength and spectral position for clusters increase with number of NPs, but clearly dimers do not disappear from view when they become embedded in larger clusters. Light scattering studies in the past have ignored this complicated optical response: focusing on either single wavelength scattering or integrated extinction is problematic.

Figure 10:
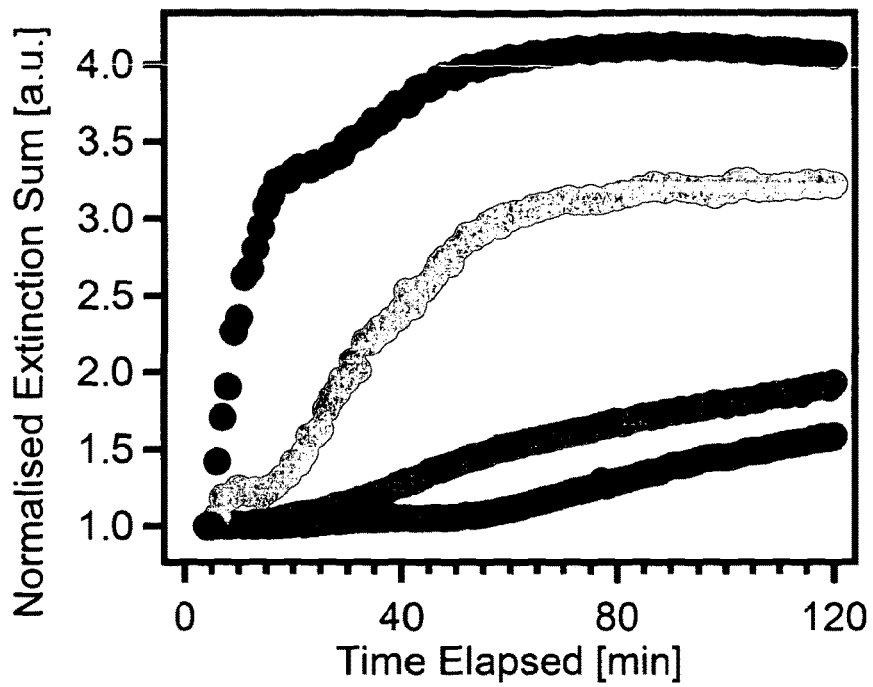
FIG. 10 (a) Shown is a spectrum of the Integrated extinction from 525 to 700 nm (normalized to t=0) for different AuNP:CB[5] ratios (as labeled). (b) Peak wavelength of the fitted coupled mode with time for the DLCA (1:80) and RLCA aggregates (1:55) of FIG. 8. Theory for linear chain of NPs also shown (dashed) using the dielectric function from Johnson and Christy with size correction.46 Illumination is perpendicular to the axis (field is parallel).
Figure 10:
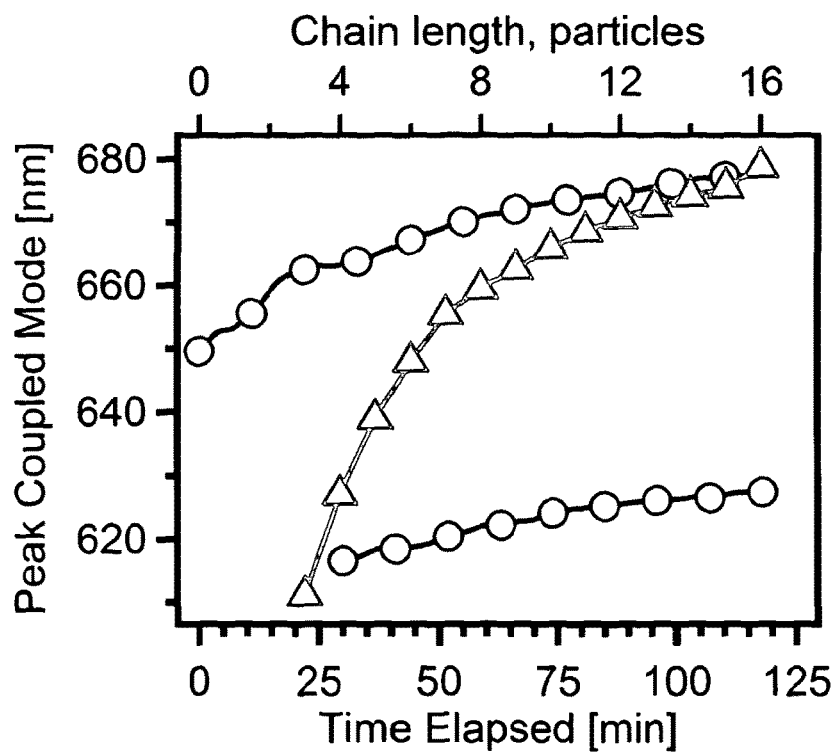

Examination of the aggregate mode peak wavelength (FIG. 10 (b)) reveals that for the quicker DLCA aggregation much greater red shifts result. We believe that this is due to the longer coupled chain lengths in different directions as compared to the compact RCLA structures (seen in TEMs, FIGS. 9 (a) and (b)). By inverting the plasmonic red shifts using the theoretical predictions (FIG. 10 (b), dashed lines), optically accessible chain lengths of approx. 10 can be inferred, within 20 min growth. In contrast to the open DLCA networks, the compact RLCA clusters show at least 5 times smaller red shifts for similar numbers of NPs in a cluster. We believe the closed RLCA topology effectively shields the embedded nanochain response (unlike embedded dimers), as indicated by our simulations. Hence it is clear that spectral shifts of the longer wavelength plasmonic modes in precisely spaced AuNP clusters give specific information about the nanoscale topology.

SERS from Plasmonic Nanojunctions

Figure 18:
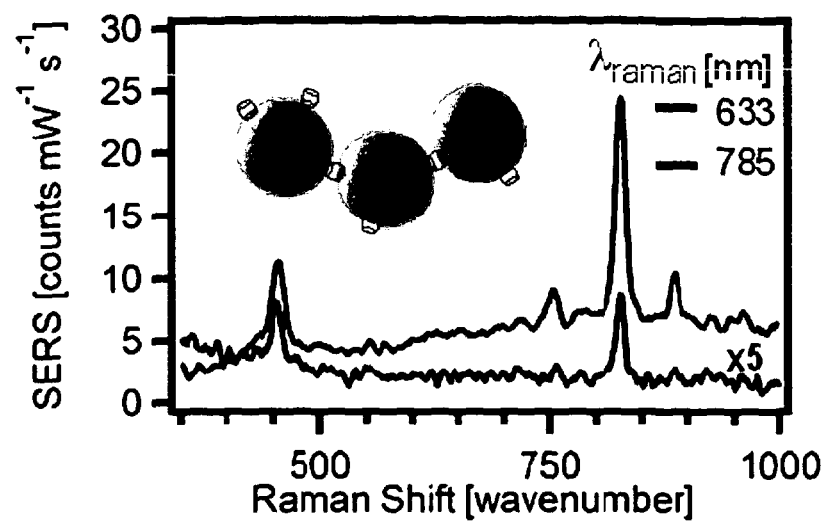
FIG. 18 is the SERS spectra of CB[5] with 633 and 785 nm laser excitation recorded in solution during aggregation with 20 nm AuNP. SERS spectra of the 1:80 AuNP:CB[5] under excitation at 633 and 785 nm acquired at the maximal plasmonic enhancement. The CB[5] fingerprint modes at 450 and 826 cm$^{-1}$ are most prominent. Acquisition time: 10 s; incident power on sample at 633 nm: 5 mW and at 785 nm: 20 mW.

As discussed, CB[5] both induces aggregation as well as defines the precise junction separation between two or more AuNPs from its rigid "barrel-shaped" geometry. It is well-known that molecules in such nanogaps between closely coupled nanoparticles experience the most intense field concentration and therefore dominate the SERS spectrum. Since cucurbit[5]urils are Raman-active and the CB[5] cage (which can harbour analyte molecules) is in this most favourable position at the centre of a hot spot, and within a nanometer of the Au surface, the AuNP:CB[5] system is a good candidate for a self-calibrated SERS substrate. For the 20 nm AuNPs especially employed here, the dimer mode is found at 590 nm and the resonant chain modes at ~650 nm, suitable for resonant excitation by 633 nm light (note the spectral positions can be tuned using different AuNP diameters). The CB[5] molecules thus act as local reporters of the optical near-field, and so simultaneous SERS measurements are recorded at different laser excitation wavelengths to understand the effect of resonance matching with the plasmon modes and also to correlate the results with observed far-field extinction. Representative SERS spectra of CB[5] with 633 and 785 nm laser excitation recorded in solution while aggregating 20 nm AuNP are shown in FIG. 18. The two signature peaks of CB[5] at 454 and 826 cm$^{-1}$ are clearly seen with both of these laser wavelengths.

We note that the citrate peaks from the AuNP capping layer are never observed in SERS on mono-disperse colloids, clearly suggesting that aggregation and selective molecular placement are required for SERS under these measurement conditions. By measuring the Raman from a known CB[5] solution under similar acquisition conditions, we calculate the bulk (or ensemble-average) enhancement factor (EF) of the AuNP:CB[5] aggregates to be $$EF=(I_{SERS} \times N_{Raman})/(I_{Raman} \times N_{SERS})=1 \times 10^7$$

where I is the intensity of the signal and N is the number of molecules in the focal volume (concentration×focal volume). The spectra were acquired using the same numerical aperture objective, hence the above expression effectively becomes $(I_{SERS} \times C_{Raman})(I_{Raman} \times C_{SERS})$ where C is the concentration of the solution used in the two cases. Since only a small fraction of the CB[5] introduced acts to define the hot spot junctions that contribute to the SERS, the local enhancement factor is expected to be much greater. Based on known fractal dimension estimates for aggregation in the DLCA case (Lin et al. *Phys. Rev. A* 1990, 41, 2005; Lin et al. *Phys. Condens. Matter* 1990, 2, 3093; Meakin. *Phys. Scr.* 1992, 46, 295), we find that less than 0.01% of the initial amount of CB[5] defines the junctions of the aggregates in the focal volume, which gives an enhancement factor of $10^{11}$. Thus the Raman enhancement recorded corresponds to the huge field confinement within the nanopair junctions. In contrast to typical methods of preparing SERS NP aggregates, these SERS enhancements are robust and repeatable.

The plasmon kinetics during aggregation are markedly different for the RLCA and DLCA growth regimes (FIG. 8). The SERS enhancements produced by the AuNP:CB[5] aggregate are thus also expected to show sensitivity to growth kinetics. The CB[n] molecule acts as a local SERS reporter itself, allowing this to be studied. Thus the SERS signals (at the 826 $cm^{-1}$ peak) from the CB[5]-mediated aggregates are simultaneously acquired (FIG. 11) from the solutions studied in FIG. 2. The SERS is normalized to counts per milliwatt per CB[5] molecule to allow comparison between the two regimes. Note that not all CB[5] in solution can contribute to the observed SERS. The measured extinction of the aggregates at the different excitation wavelengths is overlaid on the correspondingly induced SERS (FIGS. 11 (*a*) and (*b*)). The aggregate topology has a clear effect on the SERS, with the DLCA showing more than 10-fold improvement over the RLCA at 633 nm.

Similar to their rapid rise in extinction, the DLCA AuNP: CB[5] aggregates excited at 633 nm (FIG. 11 (*a*)) show immediate strong SERS signals. This arises from resonant matching of maximal plasmonic coupling with the Raman excitation wavelength following dimer and short chain-led aggregation. After 30 min, the extinction saturates but the SERS starts to drop. This difference can be understood from the spectra (FIG. 8 (*a*)) showing the resonant chain mode red-shifting away from the excitation laser, thus moving the aggregate off-resonance. Since the dimer population remains constant in this phase (FIG. 2*e*), this implies that chain modes contribute additionally to the SERS response, and the red-shifting decreases this contribution. The RLCA aggregate, however, reveals a constant increase in extinction following plasmonic coupling which keeps the aggregate band close to the Raman wavelength (FIG. 5*b*). This in turn leads to a steady increase in the SERS.

Figure 11:
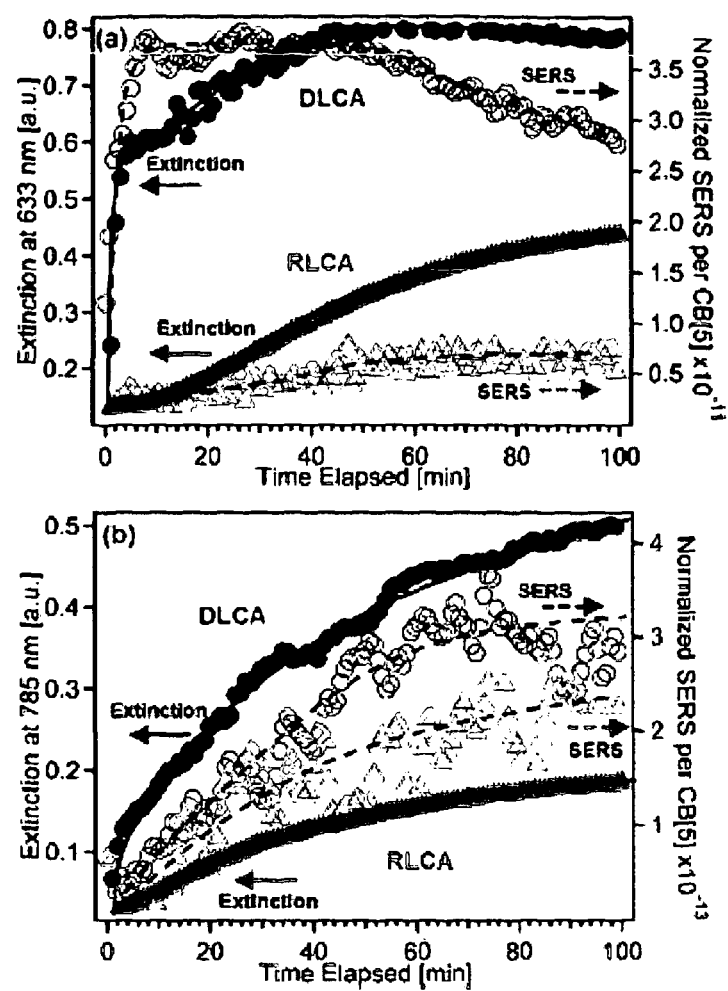
FIG. 11 shows the time-resolved normalized SERS intensity spectra of the 826 cm$^{-1}$ CB[5] Raman mode vs time for excitation wavelengths of (a) 633 and (b) 785 nm, correlated with aggregate extinction at the excitation wavelength.

While the behaviour of the SERS strengths and extinction cross sections in FIGS. 11 (*a*) and (*b*) is clearly related, the SERS is dependent on the fourth power of the local field generated at the clusters. This makes quantitative comparison between SERS and extinction less straightforward. The DLCA/RLCA SERS ratio varies as the clustering process evolves at 633 nm (as observed in FIG. 11 (*a*)). However, a systematically larger SERS signal is always obtained for the DLCA compared to RLCA clusters. This is consistent with preliminary model calculations for the near-field in open and compact clusters, respectively. More strikingly, the aggregates show hundred-fold stronger SERS at 633 nm compared to 785 nm. This is a consequence of the nonresonant situation at 785 nm. Despite the significant extinction at these longer wavelengths, the SERS is much weaker.

Nevertheless, since the strength of SERS depends on the near-field generated at the clusters, in this non-resonant situation, a lightning rod effect (Moskovits et al. *J. Phys. Chem. B* 2005, 109, 14755) is produced contributing to the weaker but still significant SERS signal. This effect is present for both DLCA and RLCA situations and may be the origin of their similar SERS signals at this longer wavelength. In summary, the CB-reported SERS potential of AuNP:CB[5] aggregate near-fields is shown to be closely related to their easily measured far-field extinction spectra, which also allows SERS to be optimized by simple far-field measurements. The SERS extracted from AuNP:CB[5] aggregate substrates can be finely tuned both temporally and energetically as a function of the CB[5] concentration via the growth kinetics, in a completely consistent manner. Thus SERS is an additional sensitive probe of nanoscale architectures in noble-metal NP:CB composites.

Host-Guest SERS

Figure 12:
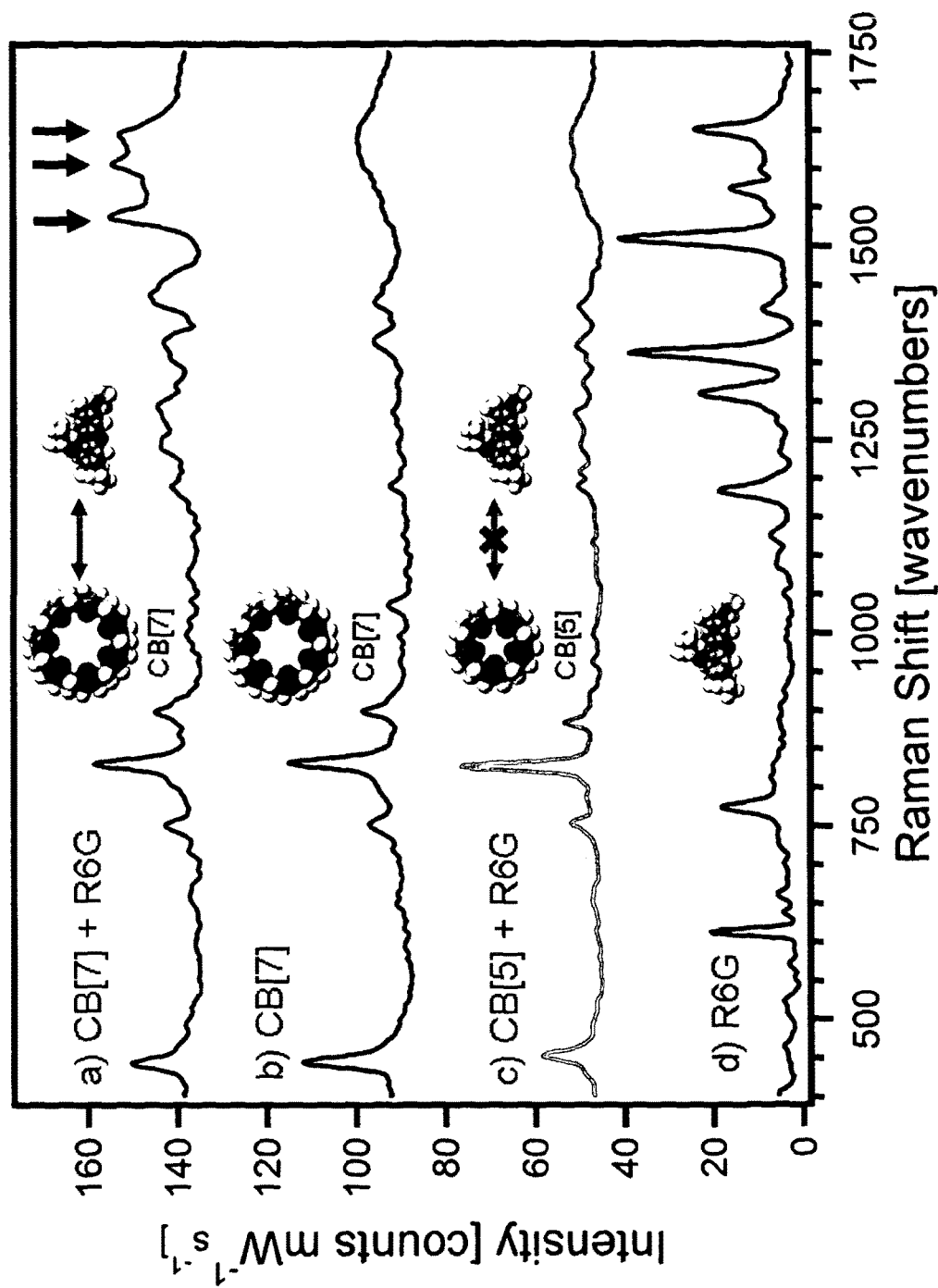
FIG. 12 shows the SERS spectra (a) CB[7] with R6G, (b) CB[7] alone, and (c) CB[5] with R6G are shown. A bulk Raman spectrum of R6G is shown in (d). Single molecules of R6G sequester in the cavity and get exposed to the intense optical fields on binding with CB[7] but not with CB[5]. Signals from R6G (marked by arrows) are clearly visible with CB[7] and absent with CB[5]. The concentrations of CB[n] and R6G were approx. micromolar and nanomolar, respectively. The spectra are baseline corrected and offset for clarity.

Besides the interesting plasmonic properties arising out of the use of cucurbit[n]urils as precise "molecular glue", their host-guest chemistry can be harnessed in sensing applications. Here we employ the host-guest properties of cucurbit[n]urils for molecular-recognition-based SERS sensing. We demonstrate this principle with the dye rhodamine 6G (R6G). A slightly larger water-soluble homologue cucurbit[7]uril has been shown to form a strong 1:1 inclusion complex with R6G with a high association constant (>50 000 $M^{-1}$) (Mohanty et al. *Angew. Chem.* 2005, 117, 3816), whereas the smaller CB[5] cannot accommodate any portion of R6G. Binding to the Au surface through the portal groups (Lee et al. *Chem. Commun.* 2010, 2438), CB[7] can thus be used to capture and expose the guest molecule to the intense optical field when used to aggregate Au nanoparticles. FIG. 12*a* shows the Raman modes of R6G (marked with arrows) inside the AuNP:CB[7] aggregates. Such modes are clearly absent in the case of AuNP:CB[5] aggregates (FIG. 12*c*), confirming the specificity of cucurbit[n]urils for the host-guest binding. For comparison, a bulk Raman spectrum of R6G is shown in FIG. 12*d*. The absence of lower wavenumber Raman modes from R6G is understood to be due to the restriction of specific modes of vibration due to the cavity binding.

In these experiments, 5 μM CB[7] was used and was mixed with 100 nM R6G. The resulting solution was then missed with 40 nm diameter gold nanoparticles to form an aggregation. Strong SERS signals were visible within 10 min. The same procedure was repeated with CB[5] and, although the aggregation proceeded in a similar way, there was no SERS signal because R6G was not exposed to hotspots. For recording SERS a 633 nm laser was used with 10 s acquisition time.

This exemplar result shows the potential of this SERS-based selective assay. We have tested our host-guest sensing approach with AuNP:CB[n] SERS substrates with other molecules, the results of which will be communicated separately. Nevertheless, it is evident that the wide range of guests for cucurbit[n]urils opens up the exciting possibility of multifunctional solution-based selective self-calibrated SERS sensors.

Experimental—Cucurbituril Guest-Host Complexes

In the following examples, the analyte (the guest) was used at a concentration of ca. 250 nM with CBs (method a.) or with 60 nm gold nanoparticles (method d.) in a cuvette. SERS signals were recorded with a 785 laser on a SE1000 Raman machine with 10-30 s acquisition time. The experimental method involves the following:

1. A cucurbituril solution was intimately mixed (using a sonicator or a vortex mixer etc. for 2-30 minutes) with an analyte solution and then added to a gold nanoparticle solution. The cucurbituril concentrations are in the micromolar range (usually 1-5 μM) however, the analyte can vary from nM (or even lower) to µM. The cucurbituril concentrations are chosen so that aggregation proceeds to produce the assembly which has its resonance with the laser in about 2-10 minutes. The concentrations of cucurbituril are those corresponding to the DLCA regime.

2. A variant of the method 1, wherein the cucurbituril and analyte mixture is added to a concentrated gold nanoparticles to the solution. The final concentration of gold particles is pM to uM depending on the size of the nanoparticles. The aggregation proceeds quickly and signals are recorded within few minutes of the mixing. This method is more suitable for developing analytical protocols.

3. The gold nanoparticle solution is mixed with a cucurbituril solution such that their final concentration is in the range 1-5 µM (as above). The analyte solution is subsequently added after 1-2 minutes, and signals are recorded usually within 10 minutes.

4. The nanoparticles may be first mixed with the analyte solution (at the desired detection level; nM to µM). The analyte molecules do not cause aggregation by themselves as confirmed by extinction measurements. Then the cucurbituril solution is added at the micromolar level and the aggregation starts. The cucurbituril encapsulates (fully or partly) the analyte molecules and SERS signals are seen within 1-10 min.

CB-AuNPs for SERS Detection

Figure 13:
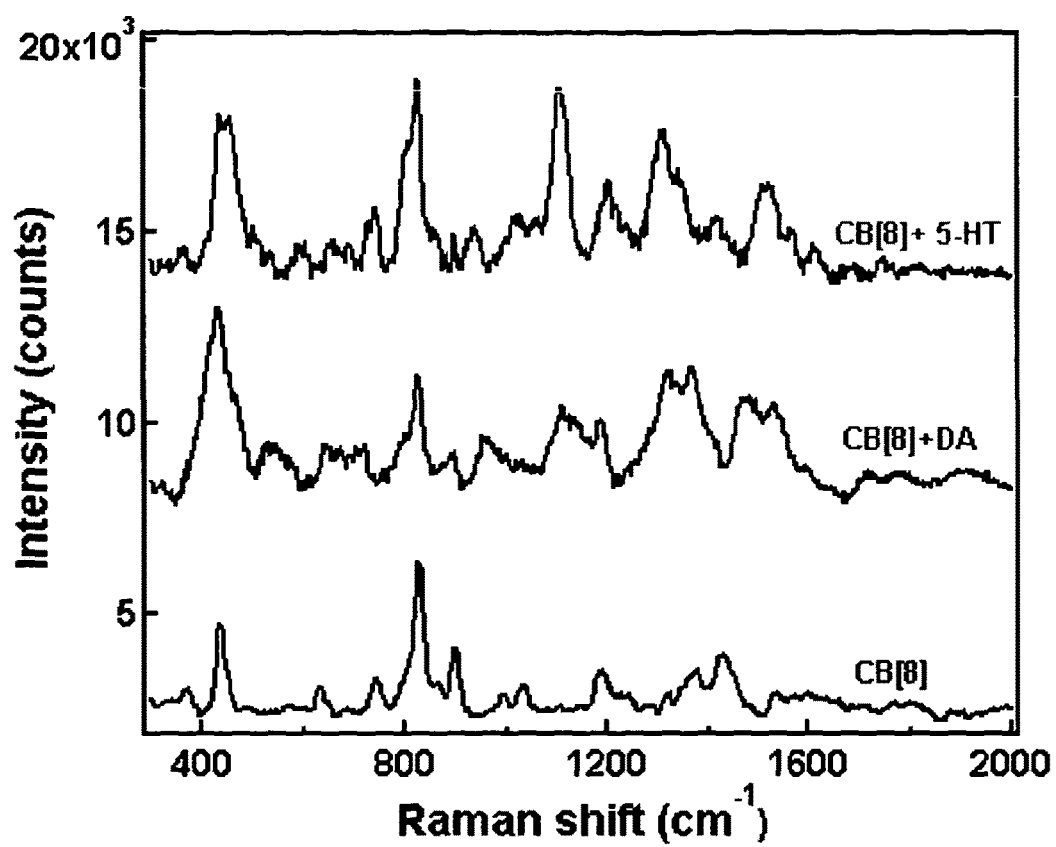
FIG. 13 shows the SERS spectra of CB[8]-AuNP system alone (bottom line) and with DA (middle line) and 5-HT (top line) showing that these molecules are bound to CB[8], and detectable by SERS.

CBs can be used not only for controlled aggregation of gold nanoparticles but also to trap molecules and expose them to intense electric fields between nanoparticles for high SERS signals. This aspect clearly has many applications in developing chemical sensors. We have been targeting the detection of certain neurotransmitters such as dopamine (DA) and serotonin (5-HT) and have tested both CB[7] and CB[8] for sequestering these molecules inside them. We can obtain SERS signals at extremely low concentrations reaching ~10-100 nM. Representative SERS spectra are shown for CB[8] sequestering DA and 5-HT in FIG. 13. Similar SERS results are obtained with CB[7] as it can also accommodate DA and 5-HT.

Increasing Selectivity of SERS Detection

Figure 14:
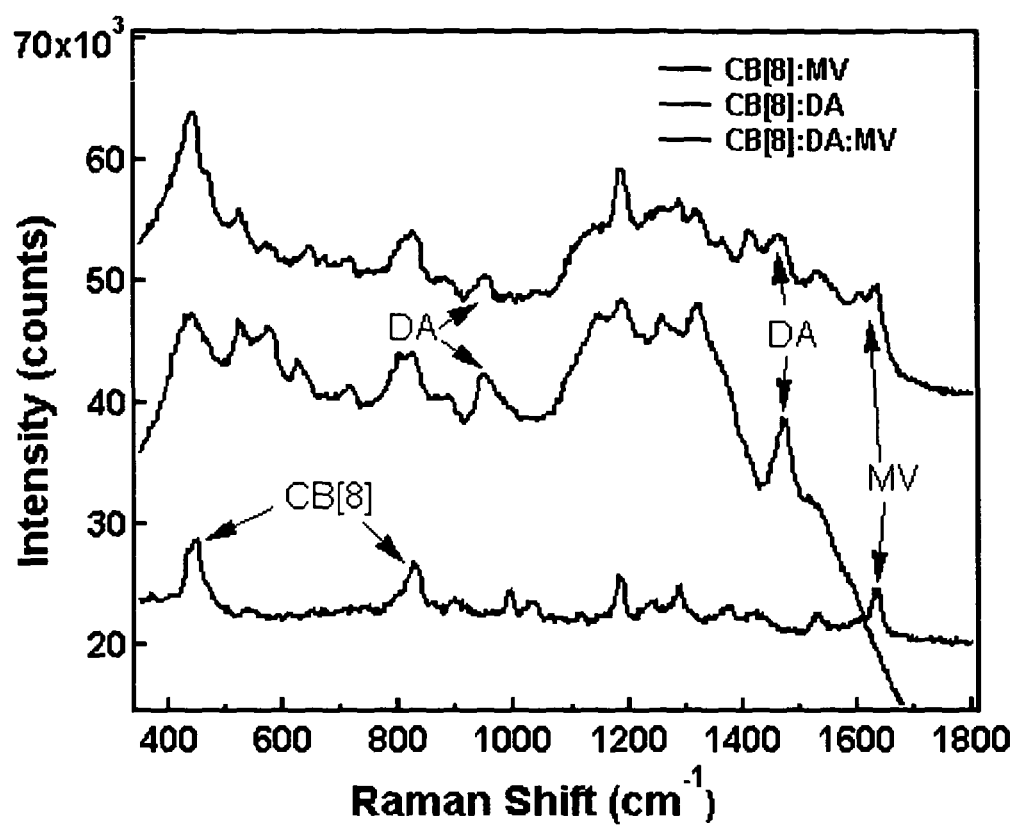
FIG. 14 shows the SERS spectra with CB[8]-AuNP system with MV as the first guest (bottom line) and with DA (middle line). The spectrum with both MV and DA (top line) shows the characteristic peaks of both two guests, here MV and DA (as indicated by the arrows), are independently detectable with SERS.

Due to its large cavity, CB[8] can bind two guests simultaneously. This offers the unique possibility of tuning the selectivity to detect the second guest by choosing an appropriate first guest. This concept can be harnessed with CB[8]-AuNP assemblies as well. Preliminary results with methylviologen (MV) as the first guest have yielded promising results in that we can detect DA (second guest) with SERS using the CB[8]:MV-AuNP complex. Typical SERS spectra are shown in FIG. 14.

Binding Curves

Figure 15:
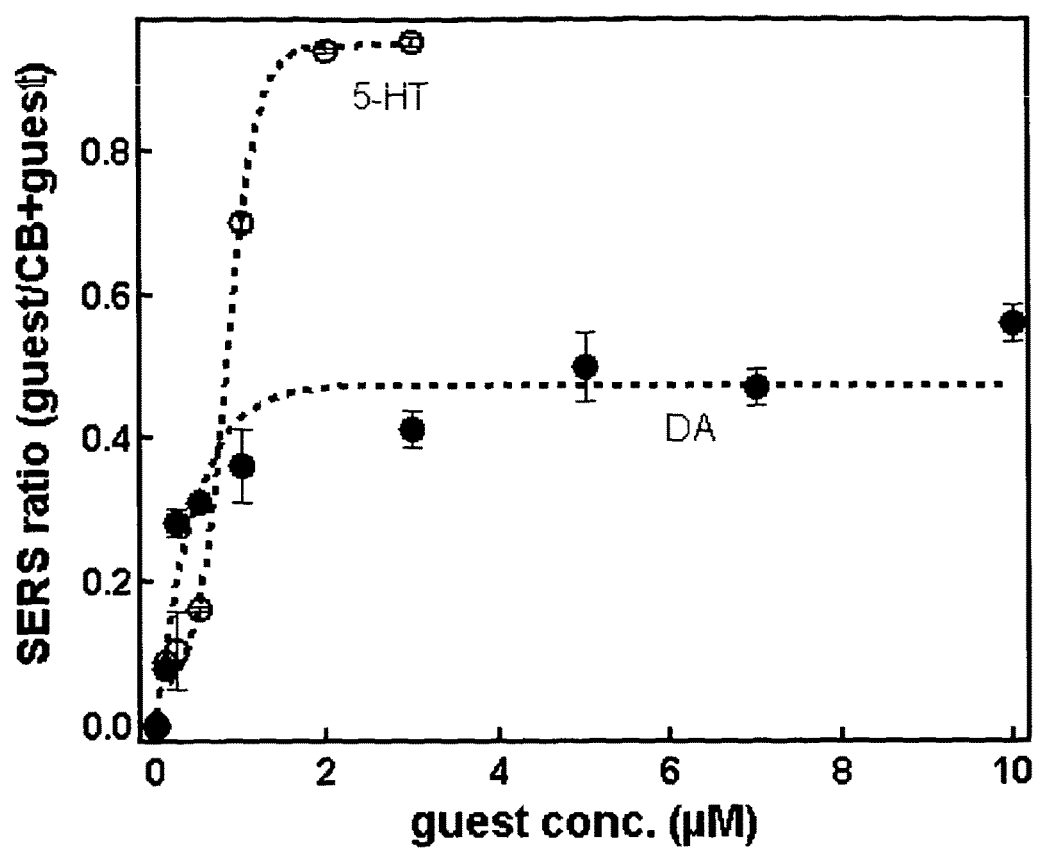
FIG. 15 shows the binding curves for 5-HT and DA determined from SERS measurements of CB[8]-AuNP with various concentrations of the respective analytes.

Apart from the ability to detect and selectively sense molecules by SERS, CB-AuNP assemblies can be used to determine the binding ability of molecules directly by SERS. CB vibrations are perturbed by the encapsulation of the guest molecules. These slight differences between the vibrational frequency of 'empty' and 'occupied' CB can be used to determine the binding affinity of the guest with CB-AuNP complex. Representative binding curves for DA and 5-HT are shown in FIG. 15. The analysis of these binding curves gives the binding constant, determined to be of the order of approx. $10^5$ $M^{-1}$ for the two cases. It also gives the relative binding strength, that 5-HT binds nearly twice as strongly as DA with CB[8]-AuNP system.

Moreover, this strategy also works with second guests. We have results with CB[8]:MV-AuNP system but this is SERS method for such determination is generic and applicable for finding the binding affinity of the second guest with any CB:first guest-AuNP system.

Furthermore, normally SERS of hydrophobic molecules is difficult as most colloidal nanoparticle suspensions are aqueous. Hence, they are not readily adsorbed on colloidal suspensions and therefore it is almost impossible to detect them by SERS. However, with the CB:AuNP system, since CBs can also sequester hydrophobic molecules (because the internal cavity is hydrophobic) the possibility of detecting them at sensitive levels with SERS is feasible. This is an added advantage of the CB:AuNP SERS detection system.

REFERENCES

All documents mentioned in this specification are incorporated herein by reference in their entirety.

Albrecht et al. *J. Am. Chem., Soc.* 1977, 99, 5215.
An et al. *Chem. Commun.* 2008, 1989.
Asian et al. *J. Phys. Chem. B* 2004, 108, 15631; Feldheim *Electrochem. Soc. Interface* 2001, 22.
Aslan et al. *Anal. Chem.* 2005, 77, 2007.
Bernard et al. *J. Phys. Chem. C* 2007, 111, 18445.
Bush, M. E. et al *J. Am. Chem. Soc.* 2005, 127, 14511-14517.
Corma et al. *Tetrahedron Lett.* 2007, 48, 4613.
Creighton *Surface Enhanced Raman Scattering*; Chang, R. K., Furtak, T. E., Eds.; Plenum: New York, 1982; p 315.
Dammer et al. *Phys. Chem. Chem. Phys* 2009, 11, 545.
Daniel et al. *Chem. Rev.* 2004, 104, 293; Alu et al. *Phys. Rev. B* 2006, 74, 2054361
De Waele et al. *Nano Lett.* 2007, 7, 2004; Harris et al. *J. Phys. Chem. C.* 2009, 113, 2784;
Fleischmann et al. *Chem. Phys. Lett.* 1974, 26, 442
Frens *Nature Phys. Sci.* 1973, 241, 20.
Ghosh et al. *Chem. Rev.* 2007, 107, 4797;
Graham *Angew. Chem., Int. Ed.* 2010, 49, 2
Hao et al. *J. Chem. Phys.* 2004, 120, 357; Kneipp et al. *Phys. Rev, Lett.* 1997, 78, 1667.
Jarvis et al. *Anal. Bioanal. Chem.* 2010, 397, 1893
Jeanmaire et al. *J. Electroanal. Chem.* 1977, 84, 1;
Jiao et al. *Chem. Commun.* 2010, 46, 2007;
Kim et al. *J. Am. Chem. Soc.* 2000, 122, 540
Klar *Biosensing with Plasmonic Nanoparticles.* In Nanophotonics with Surface Plasmons; Shalaev, V. M., Kawata, S., Eds.; Elsevier: Amsterdam, 2007; pp 253;
Kreibig et al. *Optical Properties of Metal Clusters*; Toennies, J. P., Ed.; Springer: Berlin, 1995; p 23.;
Lagona et al. *Angew. Chem., Int. Ed.* 2005, 44, 4844
Lal et al. *Chem. Soc. Rev.* 2008, 37, 898;
Lee et al. *Chem. Commun.* 2010, 2438
Lee et al. *Chem. Commun.* 2010, 46, 2438
Li et al. *Nano Lett.* 2009, 9, 485;
Liebsch et al. *J. Phys. C: Solid State* 1983, 16, 5375
Lie t al. *Chem. Mater.* 1999, 11, 23;
Lim et al. *Nat. Mater.* 2010, 9, 60; Nie et al. *Science* 1997, 275, 1102;
Lin et al. *Phys. Condens. Matter* 1990, 2, 3093; Meakin. *Phys. Scr.* 1992, 46, 295
Lin et al. *Phys. Rev. A* 1990, 41, 2005;
Lin et al. Universal Diffusion-Limited Aggregation. *J. Phys.: Condens. Matter* 1990, 2, 3093
Lin et al. Universal Reaction-Limited Colloid Aggregation. *Phys. Rev. A* 1990, 41, 2005;
Mahajan et al. *Phys. Chem. Chem. Phys.* 2010, 12, 10429;
Maier *Plasmonics Fundamentals and Applications*; Springer: New York, 2007; p 162;

Bohren et al. *Absorption and Scattering of Light by Small Particles*; Wiley-Interscience: New York, 1983; pp 75
Marquez, et al. *IEEE Trans. Nanobiosci.* 2004, 3, 39;
Martin et al. *Langmuir* 2010, 26, 7410.
Matsushita *The Fractal Approach to Heterogeneous Chemistry*, Avnir, D., Ed.; Wiley: New York, 1989; p 161
Meakin Aggregation Kinetics. *Phys. Scr.* 1992, 46, 295
Meakin The Fractal Approach to Heterogeneous Chemistry; Avnir, D., Ed.; Wiley: New York, 1989; p 131;
Mohanty et al. *Angew. Chem.* 2005, 117, 3816;
Moskovits et al. *J. Phys. Chem. B* 2005, 109, 14755
Moskovits et al. *J. Phys. Chem. B* 2005, 793 109, 14755)
Moskovits *Rev. Mod. Phys.* 1985, 57, 783.
Myers *Surfaces, Interfaces and Colloids*; Wiley-VCH: New York, 1999; Chapters 4, 5, and 10.
Myroshnychenko et al. *Chem. Soc. Rev.* 2008, 37, 1792.
Norman et al. *J. Phys. Chem. B* 2002, 106, 7005.
Novotny et al. Principles of Nano-Optics; Cambridge University Press: Cambridge, UK, 2006; pp 378-419.
Park et al. *J. Phys. Chem. B* 2006, 110, 12673.
Quinten *J. Clust. Sci.* 1999, 10, 319.
Rodriguez-Lorenzo et al. *J. Am. Chem. Soc.* 2009, 131, 4616.
Schwartzberg et al. *J. Phys. Chem. B* 2004, 108, 19191.
Scott *J. Phys. Chem.* 1996, 100, 16502.
Sztainbuch *J. Chem. Phys.* 2006, 125, 1.
Le et al. *Chem. Phys. Lett.* 2004, 396, 393.
US 2009/0273779
Weitz et al. *Phys. Rev. Lett.* 1984, 52, 1433; Girard et al. *Phys. Rev. Lett.* 2006, 97, 100801;
Wustholz et al. *J. Am. Chem. Soc.* 2010, 132, 10903;
Xu et al. *Phys. Rev. Lett.* 1999, 4357; Xu et al. *Phys. Rev. E* 2000, 62, 4318;

The invention claimed is:

1. A method for the detection of an analyte, the method comprising the steps of:
   (i) providing a test sample to be tested for the presence of an analyte;
   (ii) contacting the test sample with a linking compound, which compound is suitable for linking surfaces, thereby to permit the linking compound to bind to analyte, where present; wherein the linking compound is a host, the host being a cucurbituril compound;
   (iii) subsequently providing a plurality of surfaces, and permitting the linking compound, optionally together with any analyte to which it is bound, to form a construct of linked surfaces, where the link is formed by a linker providing a constant inter-surface separation between the linked surfaces, wherein at least one of the surfaces is the surface of a nanoparticle, and each surface is suitable for providing a surface enhanced resonance effect; and
   (iv) analysing the formed construct by a surface enhanced spectroscopic technique, thereby to detect the presence of any analyte bound to the linking compound;
   or:
   (i) providing a test sample to be tested for the presence of an analyte;
   (ii) contacting the test sample with a construct of linked surfaces, where the link is formed by a linker providing a constant inter-surface separation between the linked surfaces, wherein the linker comprises a linking compound, at least one of the surfaces is the surface of a nanoparticle, and each surface is suitable for providing a surface enhanced resonance effect; wherein the linking compound is a host, the host being a cucurbituril compound;
   (iii) permitting the linking compound to bind to analyte, where present; and
   (iv) analysing the formed construct by a surface enhanced spectroscopic technique, thereby to detect the presence of any analyte bound to the linking compound.

2. The method of claim 1, wherein the cucurbituril compound is selected from the group consisting of CB[5], CB[6], CB[7], CB[8], CB[10], and CB[12].

3. The method of claim 1, wherein the analyte, where present, is suitable for forming a guest-host complex with the cucurbituril compound.

4. The method of claim 1, wherein both surfaces are the surfaces of nanoparticles.

5. The method of claim 1, wherein the nanoparticle is a gold nanoparticle (AuNP).

6. The method of claim 1, wherein the nanoparticle has a diameter in the range 1 to 100 nm.

7. The method of claim 1, wherein the surface enhanced spectroscopy is surface enhanced Raman spectroscopy (SERS).

* * * * *